United States Patent
DeFord et al.

(10) Patent No.: US 11,712,237 B1
(45) Date of Patent: Aug. 1, 2023

(54) ANATOMICAL TISSUE ANCHOR AND RELATED METHODS

(71) Applicant: Samothrace Medical Innovations, Inc., Mount Pleasant, SC (US)

(72) Inventors: John A. DeFord, Daniel Island, SC (US); Krasnodar Ivancev, Lund (SE)

(73) Assignee: Samothrace Medical Innovations, Inc., Mount Pleasant, SC (US)

( * ) Notice: Subject to any disclaimer, the term of this patent is extended or adjusted under 35 U.S.C. 154(b) by 0 days.

(21) Appl. No.: 17/972,216

(22) Filed: Oct. 24, 2022

Related U.S. Application Data

(60) Provisional application No. 63/390,865, filed on Jul. 20, 2022.

(51) Int. Cl.
*A61B 17/04* (2006.01)
*A61B 17/00* (2006.01)

(52) U.S. Cl.
CPC ............. *A61B 17/0401* (2013.01); *A61B 2017/00818* (2013.01); *A61B 2017/00867* (2013.01); *A61B 2017/0409* (2013.01); *A61B 2017/0411* (2013.01); *A61B 2017/0417* (2013.01); *A61B 2017/0464* (2013.01)

(58) Field of Classification Search
CPC .......... A61B 2017/00818; A61B 2017/00867; A61B 2017/0409; A61B 2017/0411; A61B 2017/0417; A61B 2017/0464
See application file for complete search history.

(56) References Cited

U.S. PATENT DOCUMENTS

| | | | | |
|---|---|---|---|---|
| 5,122,122 A | * | 6/1992 | Allgood | A61B 17/34 604/105 |
| 5,496,332 A | * | 3/1996 | Sierra | A61B 17/0057 606/139 |
| 5,716,369 A | * | 2/1998 | Riza | A61B 17/34 606/139 |
| 7,004,949 B2 | * | 2/2006 | Yencho | A61B 17/11 606/155 |
| 2002/0091399 A1 | * | 7/2002 | Ben David | A61B 17/3462 606/158 |
| 2002/0151921 A1 | * | 10/2002 | Kanner | A61B 17/0057 606/151 |
| 2003/0023267 A1 | * | 1/2003 | Ginn | A61B 17/0057 606/108 |
| 2004/0220592 A1 | * | 11/2004 | Mueller | A61B 17/0057 606/151 |

(Continued)

OTHER PUBLICATIONS

Bostonscientific.com [online], "Resolution 360™ Ultra Clip" Apr. 19, 2021, retrieved on Sep. 19, 2022, retrieved from URL <https://www.bostonscientific.com/en-US/products/clips/resolution-360-ultra-clip.html>, 4 pages.

(Continued)

*Primary Examiner* — Alexander J Orkin
(74) *Attorney, Agent, or Firm* — Fish & Richardson P.C.

(57) ABSTRACT

An anatomical tissue anchor includes a central body and tissue stabilizing arms extending outwardly from the central body. The tissue stabilizing arms are spaced apart from one another. The tissue anchor has a deployed state in which the central body defines an opening configured to allow an instrument to be passed therethrough and the tissue stabilizing arms extend radially outwardly from the central body.

19 Claims, 28 Drawing Sheets

(56) References Cited

U.S. PATENT DOCUMENTS

| | | | | |
|---|---|---|---|---|
| 2007/0203507 A1* | 8/2007 | McLaughlin | ...... | A61B 17/0625 606/144 |
| 2008/0287988 A1* | 11/2008 | Smith | ...... | A61B 17/0643 606/213 |
| 2010/0217132 A1* | 8/2010 | Ellingwood | ...... | A61B 5/6862 600/481 |
| 2010/0312064 A1* | 12/2010 | Weisenburgh, II | ...... | A61B 17/3423 600/206 |
| 2012/0253386 A1* | 10/2012 | Rowe | ...... | A61B 17/02 606/213 |
| 2015/0265261 A1* | 9/2015 | Alokaili | ...... | A61B 17/7061 604/101.01 |
| 2019/0076638 A1* | 3/2019 | Dailey | ...... | A61B 17/0057 |
| 2020/0289100 A1* | 9/2020 | Miller | ...... | A61B 17/068 |

OTHER PUBLICATIONS

Cookmedical.com [online], "Cope Gastrointestinal Suture Anchor Set" Dec. 9, 2016, retrieved on Sep. 19, 2022, retrieved from URL <https://www.cookmedical.com/products/ir_gias_webds/>, 3 pages.

Ramírez-Ramírez et al., "Simplified magnetic anchor-guided endoscopic submucosal dissection: an ex vivo porcine model." Revista de Gastroenterología de México (English Edition) 87.1, Jan. 2022, 13-19 (with English abstract).

Wang et al., "Retrievable puncture anchor traction method for endoscopic ultrasound-guided gastroenterostomy: A porcine study." World Journal of Gastroenterology 26.25, Jul. 7, 2020, 3603-3610.

\* cited by examiner

ANATOMICAL TISSUE ANCHOR AND RELATED METHODS

CROSS-REFERENCE TO RELATED APPLICATIONS

This application claims priority to U.S. Application No. 63/390,865, filed on Jul. 20, 2022, which is hereby incorporated by reference in its entirety.

BACKGROUND

Open surgery is the mainstay of surgical treatment of the intestines today despite being associated with multiple risks for severe complications due to its invasive nature. Less invasive alternatives, such as laparoscopic, endoscopic bowel surgery, and percutaneous endoluminal bowel surgery, have their limitations.

Laparoscopic bowel surgery carries considerable risks in patients who have previously undergone bowel surgery or have chronic inflammatory bowel diseases and, therefore, have developed extensive adhesions that can prevent safe access to the bowel. Endoscopic bowel surgery can typically be performed only on operable lesions that can be reached from the natural orifices such as the rectum for the large bowel, or through the esophagus, through the stomach, and into the duodenum. Because of the limitations of these surgical methods, only a small portion of the small intestine is accessible for these two less invasive alternatives.

Percutaneous endoluminal bowel surgery has not been fully explored due to the lack of suitable instruments. For example, a patient with a small intestine obstruction caused by an adhesion band in a hostile abdomen would be an ideal candidate for a process involving percutaneous access to the small intestine at a location proximate to the obstruction and relief of the blockage using balloon dilation. Imaging techniques such as contrast-enhanced CT can be used to identify where the obstruction is located.

To access a particular bowel loop near the obstruction, an anchoring device can be used. A conventional anchoring device called a T-fastener consists of a short (e.g., no more than a centimeter long) piece of a wire or cannula with a suture (either resorbable or permanent) attached in its middle. Upon introduction, using a needle, the T-fastener is deployed inside the bowel, and the suture is used for pulling the T-fastener back until the T-fastener lodges against the bowel wall. The suture is stretched from the outside perpendicularly to the metallic piece of the T-fastener. The T-fastener provides limited support, and a physician may have difficulties maneuvering surgical instruments relative to the T-fastener. Once the bowel is stabilized with the T-fastener, or preferably with at least three T-fasteners forming a triangle, an additional site of access is typically required, usually placed in the center of the triangle formed by the T-fasteners, to allow entry of devices needed to treat the diseased portion of the bowel.

SUMMARY

To safely access the particular bowel loop proximate to the obstruction, there is a need for a tissue anchor that can provide safe and secure fixation of a bowel loop to continue with the next step of placement of a device for treatment or in preparation for later wound closure. This disclosure features a tissue anchor (e.g., an anchoring device or stabilizing device) that is designed to be retrievable and to be removed after placement of instruments (such as, for example, a stabilization sheath, endoscope, dilation balloon, or closure device to place a suture line around the entrance hole in the bowel wall). The tissue anchor can provide an opening through which an instrument can be inserted, thus allowing the tissue anchor to be easily used in combination with the instrument.

In one aspect, a method is featured. The method includes positioning a tissue anchor within an anatomical cavity of a patient, placing the tissue anchor in a deployed state in which the tissue anchor defines an opening, causing the tissue anchor in the deployed state to engage with a tissue wall defining the anatomical cavity to stabilize the tissue wall, delivering at least a portion of a medical instrument into the anatomical cavity with the medical instrument being aligned with the opening of the tissue anchor, and using the medical instrument to perform a medical procedure on the tissue wall or in the anatomical cavity.

In another aspect, an anatomical tissue anchor is featured. The anatomical tissue anchor includes a central body and tissue stabilizing arms extending outwardly from the central body. The tissue stabilizing arms are spaced apart from one another. The tissue anchor has a deployed state in which the central body defines an opening configured to allow an instrument to be passed therethrough and the tissue stabilizing arms extend radially outwardly from the central body.

Implementations can include one or more of the features described below and throughout this disclosure.

In some implementations, the method further includes after delivering at least the portion of the medical instrument into the anatomical cavity and before using the medical instrument to perform the medical procedure on the tissue wall or in the anatomical cavity, initiating withdrawal of the tissue anchor from the anatomical cavity such that the opening of the tissue anchor is positioned around and is moved along at least the portion of the medical instrument during the withdrawal of the tissue anchor.

In some implementations, the medical instrument is a closure device, and the medical procedure is a tissue closure procedure performed on the tissue wall.

In some implementations, delivering at least the portion of the medical instrument into the anatomical cavity with the medical instrument being aligned with the opening of the tissue anchor includes inserting the portion of the medical instrument through the opening of the tissue anchor. Using the medical instrument to perform the medical procedure on the tissue wall or in the anatomical cavity can include using the medical instrument to perform the medical procedure while the portion of the medical instrument extends through the opening of the tissue anchor.

In some implementations, the medical instrument is a surgical instrument, and the medical procedure is a surgical procedure performed in the anatomical cavity.

In some implementations, positioning the tissue anchor within the anatomical cavity includes inserting a puncture device through the tissue wall and inserting the tissue anchor through the puncture device into the anatomical cavity.

In some implementations, positioning the tissue anchor within the anatomical cavity further includes inserting a guide wire through the puncture device into the anatomical cavity. Inserting the tissue anchor through the puncture device into the anatomical cavity can include moving the tissue anchor in a collapsed state along the guide wire into the anatomical cavity.

In some implementations, inserting the guide wire through the puncture device into the anatomical cavity includes applying a force on a tip of the puncture device to cause the tip of the puncture device to form an opening and advancing the guide wire through the opening formed at the tip of the puncture device to insert the guide wire into the anatomical cavity.

In some implementations, placing the tissue anchor in the deployed state includes causing the tissue anchor to expand radially outwardly while positioning the tissue anchor in the anatomical cavity and causing the tissue anchor to form the opening.

In some implementations, causing the tissue anchor to expand radially outwardly includes causing tissue stabilizing arms to extend radially outwardly from a central body of the tissue anchor. The central body can define the opening of the tissue anchor.

In some implementations, the tissue stabilizing arms includes at least three tissue stabilizing arms.

In some implementations, causing the tissue anchor to form the opening further includes causing a central body of the tissue anchor to extend along an arc from a first lengthwise end of the central body to a second lengthwise end of the central body.

In some implementations, the method further includes withdrawing the tissue anchor from the anatomical cavity. Withdrawing the tissue anchor from the anatomical cavity can include placing the tissue anchor in a collapsed state by positioning a sheath over a retrieval member extending from the first lengthwise end or the second lengthwise end of the central body of the tissue anchor.

In some implementations, in the deployed state of the tissue anchor, the central body extends along a plane, and the retrieval member extends from the first lengthwise end or the second lengthwise end of the central body along an axis substantially perpendicular to the plane.

In some implementations, placing the tissue anchor in the collapsed state includes causing the first lengthwise end and the second lengthwise end of the central body to move away from one another, thereby causing the central body to form a straightened structure positionable in the sheath.

In some implementations, the central body extends along an axis in the collapsed state of the tissue anchor. Placing the tissue anchor in the collapsed state can include causing tissue stabilizing arms attached to the central body to extend parallel to the axis along which the central body extends in the collapsed state of the tissue anchor.

In some implementations, the method further includes after placing the tissue anchor in the deployed state and before causing the tissue anchor in the deployed state to engage with the tissue wall, enlarging a size of the opening of the tissue anchor. Enlarging the size of the opening of the tissue anchor can include inserting into the opening at least one device selected from the group consisting of: a dilator, a balloon, and a stent.

In some implementations, causing the tissue anchor in the deployed state to engage with the tissue wall includes applying a pulling force on a central body of the tissue anchor to cause the tissue anchor to be pulled against the tissue wall.

In some implementations, the pulling force is a first pulling force applied on a first lengthwise half of the central body. Causing the tissue anchor in the deployed state to engage with the tissue wall can include applying, while applying the first pulling force on the central body, a second pulling force on a second lengthwise half of the central body to cause the tissue anchor to be pulled against the tissue wall. The first pulling force and the second pulling force can be in a direction perpendicular to plane alone which the central body extends.

In some implementations, applying the pulling force on the central body to cause the tissue anchor to be pulled against the tissue wall includes pulling a control member locked to the central body via a locking wire extending along the central body. The method can further include removing the locking wire from the tissue anchor to release the control member from the central body, removing the control member from the tissue anchor, and then withdrawing the tissue anchor from the anatomical cavity.

In some implementations, the tissue anchor used in the method includes a central body and tissue stabilizing arms extending outwardly from the central body. The tissue stabilizing arms can be spaced apart from one another. In the deployed state of the tissue anchor, the central body defines the opening and the tissue stabilizing arms extend radially outwardly from the central body.

In some implementations, the central body is configured to, in the deployed state of the tissue anchor, extend along an arc from a first lengthwise end of the central body to a second lengthwise end of the central body, the tissue anchor in the deployed state defining a slot between the first lengthwise end and the second lengthwise end of the central body.

In some implementations, the tissue anchor has a collapsed state in which the central body extends from the first lengthwise end to the second lengthwise end of the central body along an axis.

In some implementations, in the collapsed state, the tissue stabilizing arms extend parallel to the axis along which the central body extends in the collapsed state of the tissue anchor.

In some implementations, a length of the central body from the first lengthwise end to the second lengthwise end of the central body is between 15 and 45 millimeters.

In some implementations, in the deployed state, the central body extends along a plane, and the tissue anchor further includes a retrieval member connected to the central body, the retrieval member configured to, in the deployed state of the tissue anchor, protrude along an axis perpendicular to the plane.

In some implementations, the retrieval member is a hollow retrieval member. The tissue anchor can further include a locking wire extending through the hollow retrieval member.

In some implementations, the tissue anchor further includes a first control member attached to a first lengthwise half of the central body and a second control member attached to a second lengthwise half the central body.

In some implementations, the tissue anchor further includes a locking wire extending along a perimeter of the central body. The locking wire can be configured to lock the first control member and the second control member to the central body.

In some implementations, the central body and the tissue stabilizing arms are formed of a shape memory material biasing the tissue anchor into the deployed state.

In some implementations, a length of each of the tissue stabilizing arms is between 2 and 10 millimeters.

In some implementations, an overall width of the tissue anchor in the deployed position is between 6 and 40 millimeters.

Implementations described in this disclosure can have one or more of the advantages described below or elsewhere in this disclosure.

Implementations can improve the ease of access to internal tissue for medical instruments. For example, a tissue anchor in these implementations can include an opening through which a medical instrument can be inserted. In addition, because the tissue anchor allows for access to the internal tissue by a medical instrument, implementations can reduce the number of access sites through the tissue wall. Rather than creating an access site for the tissue anchor and then creating a separate access site for a medical instrument, an operator can use a single access site that accommodates both the tissue anchor and the medical instrument.

Implementations can further simplify the retrieval process for a tissue anchor, thus allowing the tissue anchor to be removed from the tissue wall without a reduced risk of creating tissue adhesions. For example, the tissue anchor in implementations can include one or more structural features, e.g., sutures, pull wires, retrieval members, or other elements for retrieval of the tissue anchor from the anatomy, that allow the tissue anchor to be easily retrieved through an access site.

Furthermore, the tissue anchors in implementations can be easily deployed and manipulated. For example, a tissue anchor can include a body that can be collapsed to a small size so the tissue anchor can be placed through a small access site through a tissue wall. The body can be automatically deployed to a larger size upon being positioned in an internal patient cavity so that the body can provide a stable contact to the tissue wall. The body can be made of a shape-memory material that deforms into a deployed state after being advanced through the access port such as a needle or a sheath.

Tissue anchors in implementations can be easily manufactured. The tissue anchors, for example, can be formed of relatively few components, e.g., 5 or fewer components, and can be made from materials that are easily manufactured using mass manufacturing techniques.

Tissue anchors in implementations can more stably hold a tissue wall. The configurations of the tissue anchors offer a larger surface area for support of the bowel than conventional tissue anchors (e.g., T-fasteners). This can result in safer and more secure support.

BRIEF DESCRIPTION OF THE DRAWINGS

FIGS. 5A-5D and 5F are side sectional views of the tissue anchor system being used on anatomy, and FIG. 5E is a cross-sectional view of the tissue anchor system being used on anatomy along the section line 5E-5F in FIG. 5D.

FIGS. 6A-6D and 6F are side sectional views of the tissue anchor system being used on the anatomy of the subject, and FIG. 6E is a cross-sectional view of the tissue anchor system being used on the anatomy of the subject along the section line 6E-6E in FIG. 6D.

FIGS. 7A-7H and 7J are side sectional views of the tissue anchor system being used on the anatomy of the subject, and FIG. 7I is a cross-sectional view of the tissue anchor system being used on the anatomy of the subject along the section line 7I-7I in FIG. 7H.

DETAILED DESCRIPTION

Endoluminal surgical procedures often start with placement of a tissue anchor to control and/or stabilize an underlying tissue wall (e.g., bowel tissue) and provide a stable access location for delivery of a closure device (e.g., for deploying sutures) or another medical instrument. An instrument sheath can be introduced through the access location into an anatomical cavity, thus allowing other medical instruments (e.g. wires, balloons, catheters) and drugs to be introduced into the anatomical cavity for treating a condition (such as a bowel obstruction). Upon completion of the procedure, the instrument sheath is removed, and a closure device can be used to close the access hole in the tissue wall, e.g., after having removed the anchor device.

Figure 1:
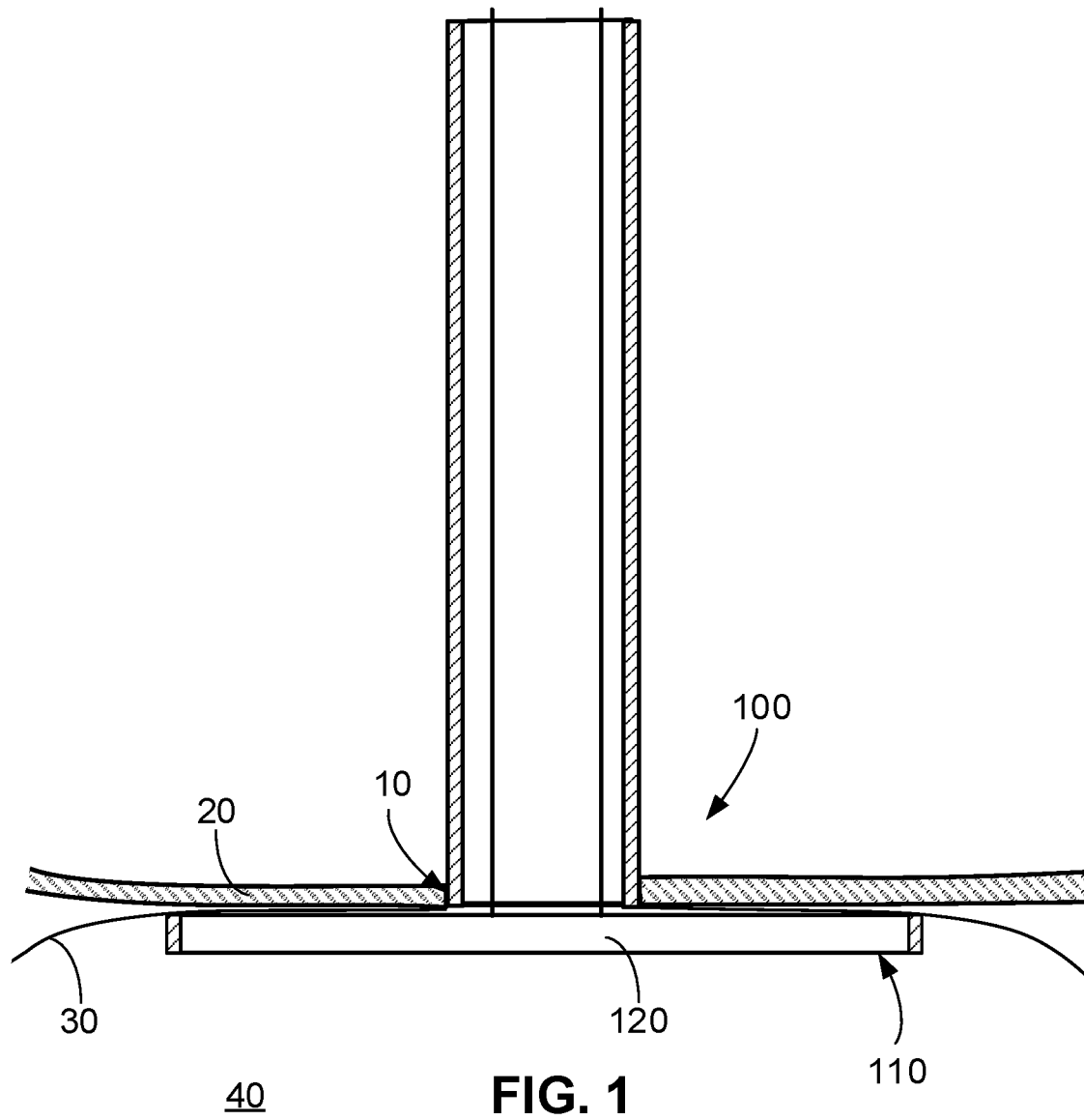
FIG. 1 illustrates an example of a tissue anchor system being used to pull an organ tissue against a tissue wall to stabilize the organ tissue.

Referring to FIG. 1, a tissue anchor system 100 includes a tissue anchor 110 that can be inserted through an access site 10 through a first tissue layer 20 (e.g., an abdominal wall) and a second tissue layer 30 (e.g., an internal tissue layer, such as an intestinal wall). The tissue anchor 110 is positioned within an anatomical cavity 40 of a patient at least partially defined by the second tissue layer 30. The tissue anchor 110 is placed in a deployed state, as shown in FIG. 1, to engage with the second tissue layer 30 and stabilize the second tissue layer 30. As illustrated in FIG. 1, the tissue anchor 110 can be used to pull the second tissue layer 30 toward the first tissue layer 20 to stabilize the second tissue layer 30. As described in this disclosure, the tissue anchor 110 can allow for access by a medical instrument through an opening 120 of the tissue anchor 110.

Example Structures of Tissue Anchors

Tissue anchors described in this disclosure can include a number of structural configurations. FIGS. 2A-2C, FIG. 3A-3D, and FIGS. 4A-4C illustrate examples of tissue anchors having differing structural configurations.

Figure 2A:
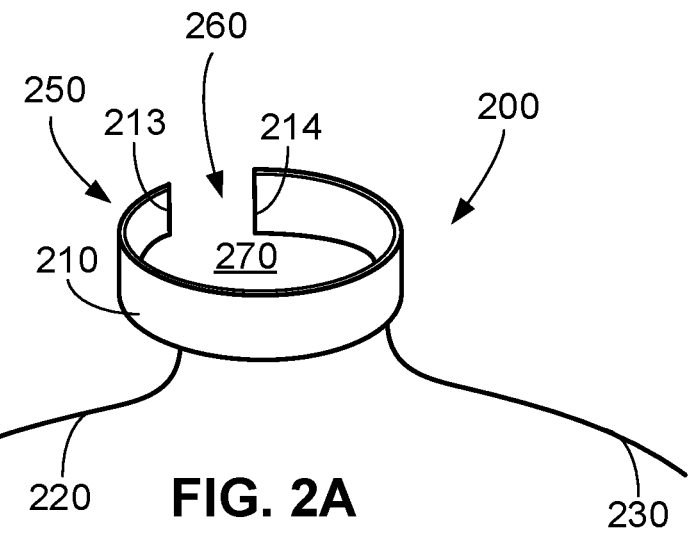
FIGS. 2A-2B are top perspective and top views, respectively, of an example of a tissue anchor system in a deployed state.
Figure 2B:
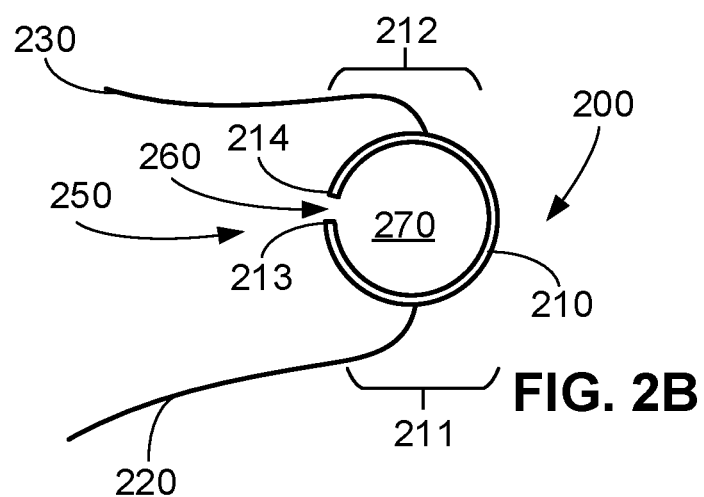
Figure 2C:
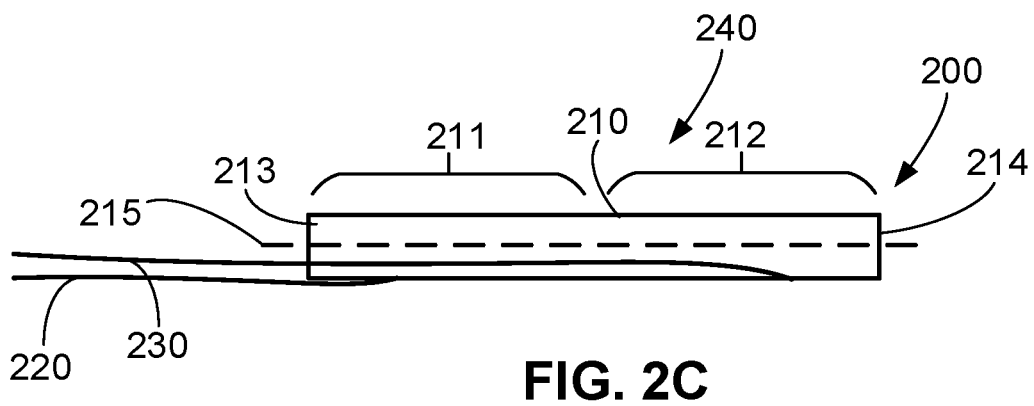
FIG. 2C is a side view of the tissue anchor system of FIGS. 2A-2B in a collapsed state.

FIGS. 2A-2C illustrate an example of a tissue anchor 200 including a central body 210. The tissue anchor 200 includes one or more control members, e.g., a control member 220 and a control member 230. The tissue anchor 200 and the central body 210 have a collapsed state 240 (FIG. 2C) and a deployed state 250 (FIGS. 2A-2B). The tissue anchor 200 can be collapsed to decrease the volume circumscribed by the tissue anchor 200, thus allowing the tissue anchor 200 to be more easily retrieved from the anatomy.

The central body 210 includes a first lengthwise half 211 and a second lengthwise half 212. The central body 210 is deformable between the deployed state 250 and the collapsed state 240. The central body 210 can be formed of a shape memory material (e.g., a shape memory alloy, a copper-aluminum-nickel alloy, a nickel-titanium alloy, 304 stainless steel, 316 stainless steel, or other appropriate shape memory material) that biases the central body 210 and/or the tissue anchor 200 into the deployed state 250.

The control member 220 is attached to the central body 210 at the first lengthwise half 211 of the central body, and the control member 230 is attached to the central body 210 at the second lengthwise half 212 of the central body 210. The control members 220, 230 can be, for example, a medical suture formed of one or more filaments, such as a polymer (e.g., nylon, polypropylene, or polyester), silk, or another appropriate suture material. The control members 220, 230 can be attached to the central body 210 in a manner that allows an operator to manipulate the tissue anchor 200 when the tissue anchor 200 is positioned within the anatomical cavity (e.g., the anatomical cavity 40 in FIG. 1).

FIG. 2C illustrates the tissue anchor 200 in the collapsed state 240 in which the central body 210 is straightened out to extend substantially along an axis, e.g., in response to an external force provided by a sheath being placed over the tissue anchor 200 as described in greater detail in this disclosure. In the collapsed state 240, the central body 210 extends from a first lengthwise end 213 on the first lengthwise half 211, substantially along an axis 215, to a second lengthwise end 214 on the second lengthwise half 212.

FIGS. 2A-2B illustrate the tissue anchor 200 in the deployed state 250 in which the central body 210 is in its neutral state. In the deployed state 250 (FIGS. 2A-2B), the central body 210 extends along a loop but does not itself form a contiguous loop. The central body 210 forms an interrupted ring. The central body 210 extends from the first lengthwise end 213 along an arc to the second lengthwise end 214. The tissue anchor 200 in the deployed state 250 defines a slot 260 between the first lengthwise end 213 and the second lengthwise end 214. The slot 260 and the configuration of the central body 210 as an interrupted ring allow the central body 210 to be enlarged, e.g., using a dilator, a balloon, or a stent. An operator can thus easily change the overall width of the central body to a desired width. The tissue anchor 200 in the deployed state 250 further defines an opening 270 that is in a central portion of the tissue anchor 200 that is shaped and sized to allow for insertion of a medical instrument.

FIGS. 3A-3D illustrate another example of a tissue anchor 300 including a central body 310. The tissue anchor 300 and its components (including the central body 310 and control members 320, 330) are identical to the tissue anchor 200 and its components except that the tissue anchor 300 further includes one or more tissue stabilizing arms, e.g., tissue stabilizing arms 380a, 380b, 380c. The tissue stabilizing arms 380a, 380b, 380c are spaced apart from one another and are further attached at locations along the central body 310 that are spaced apart from one another. The tissue stabilizing arms 380a, 380b, 380c are configured to provide tissue contact surfaces 382a, 382b, 382c at distal tips 381a, 381b, 381c of the tissue stabilizing arms 380a, 380b, 380c.

Figure 3A:
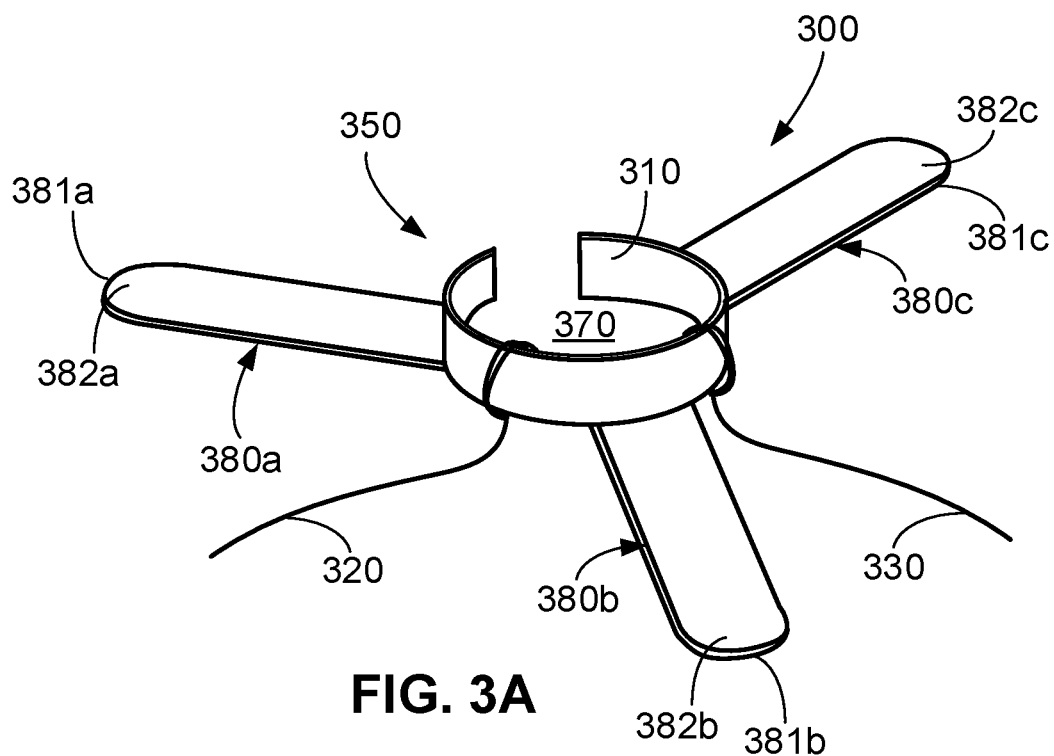
FIGS. 3A-3B are top perspective and top views, respectively, of another example of a tissue anchor system in a deployed state.
Figure 3B:
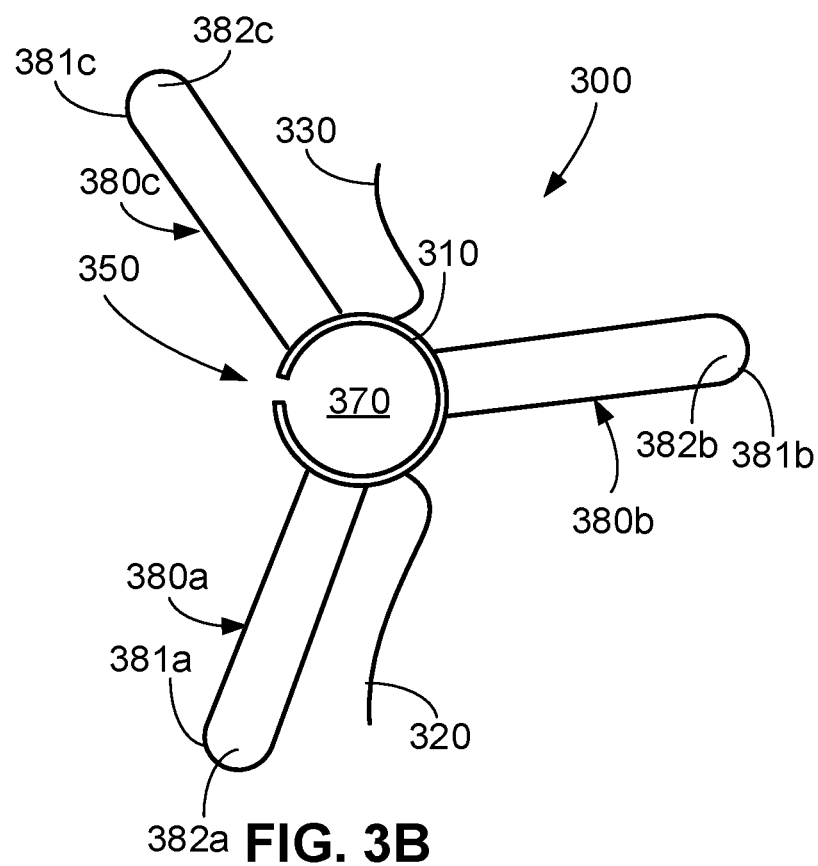
Figure 3C:
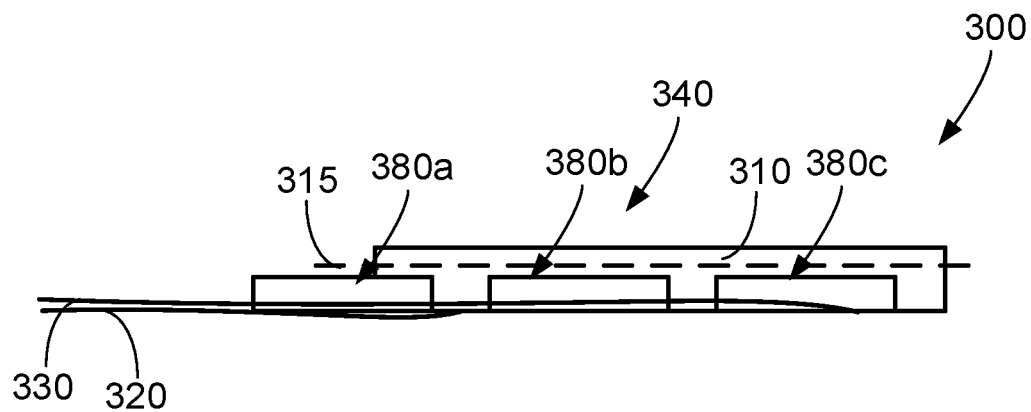
FIGS. 3C-3D are side and top views, respectively, of the tissue anchor system of FIGS. 3A-3B in a collapsed state.
Figure 3D:
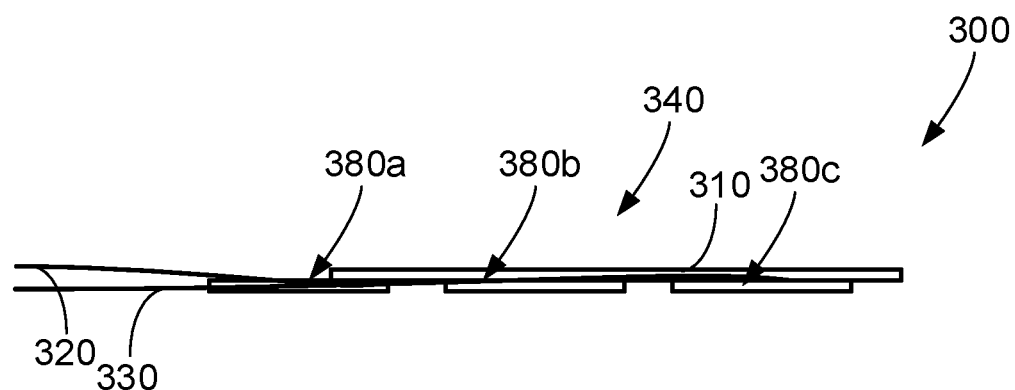

The tissue anchor 300, the central body 310, and the tissue stabilizing arms 380a, 380b, 380c have a deployed state 350 (FIGS. 3A-3B) and a collapsed state 340 (FIGS. 3C-3D). The tissue stabilizing arms 380a, 380b, 380c, like the central body 310, is formed of a shape memory material (e.g., a shape memory alloy, a copper-aluminum-nickel alloy, a nickel-titanium alloy, or other appropriate shape memory material). The tissue stabilizing arms 380a, 380b, 380c can be formed integrally with the central body 310, e.g., can be formed as part of the same sheet metal forming process. The tissue stabilizing arms 380a, 380b, 380c are formed such that tissue stabilizing arms 380a, 380b, 380c are biased toward a deployed state 350.

In the example shown in FIGS. 3A-3D in which the tissue anchor 300 includes three tissue stabilizing arms 380a, 380b, 380c, the control members 320, 330 of the tissue anchor 300 can be positioned between pairs of the tissue stabilizing arms 380a, 380b, 380c. For example, the control member 320 can be positioned between the tissue stabilizing arm 380a and the tissue stabilizing arm 380b, and the control member 330 can be positioned between the tissue stabilizing arm 380b and the tissue stabilizing arm 380c.

FIGS. 3C-3D illustrate the tissue anchor 300 in the collapsed state 340 in which the central body 310 is straightened out to extend substantially along an axis and the tissue stabilizing arms 380a, 380b, 380c are deformed to extend substantially along the axis. The tissue anchor 300 can be placed in the collapsed state 340, for example, in response to an external force provided by a sheath being placed over the tissue anchor 300 as described in greater detail in this disclosure. In the collapsed state 340 of the tissue anchor 300, the tissue stabilizing arms 380a, 380b, 380c are deformed inwardly toward the central body 310. In particular, the distal tips 381a, 381b, 381c are deformed toward the axis 315 along which the central body 310 extends in the collapsed state 340. The tissue stabilizing arms 380a, 380b, 380c extend parallel to the axis 315 along which the central body 310 extends in the collapsed state 340 of the tissue anchor 300.

FIGS. 3A-3B illustrate the tissue anchor 300 in the deployed state 350 in which the central body 310 and the tissue stabilizing arms 380a, 380b, 380c is in their neutral states. In the deployed state 350 (FIGS. 3A-3B) of the tissue anchor 300, the tissue stabilizing arms 380a, 380b, 380c extend radially outwardly from the central body 310 and from the opening 370 of the tissue anchor 300. The tissue stabilizing arms 380a, 380b, 380c can be equally spaced apart from one another in the deployed state 350 though as described elsewhere in this disclosure, the spacing between tissue stabilizing arms may vary in implementations.

Figure 4A:
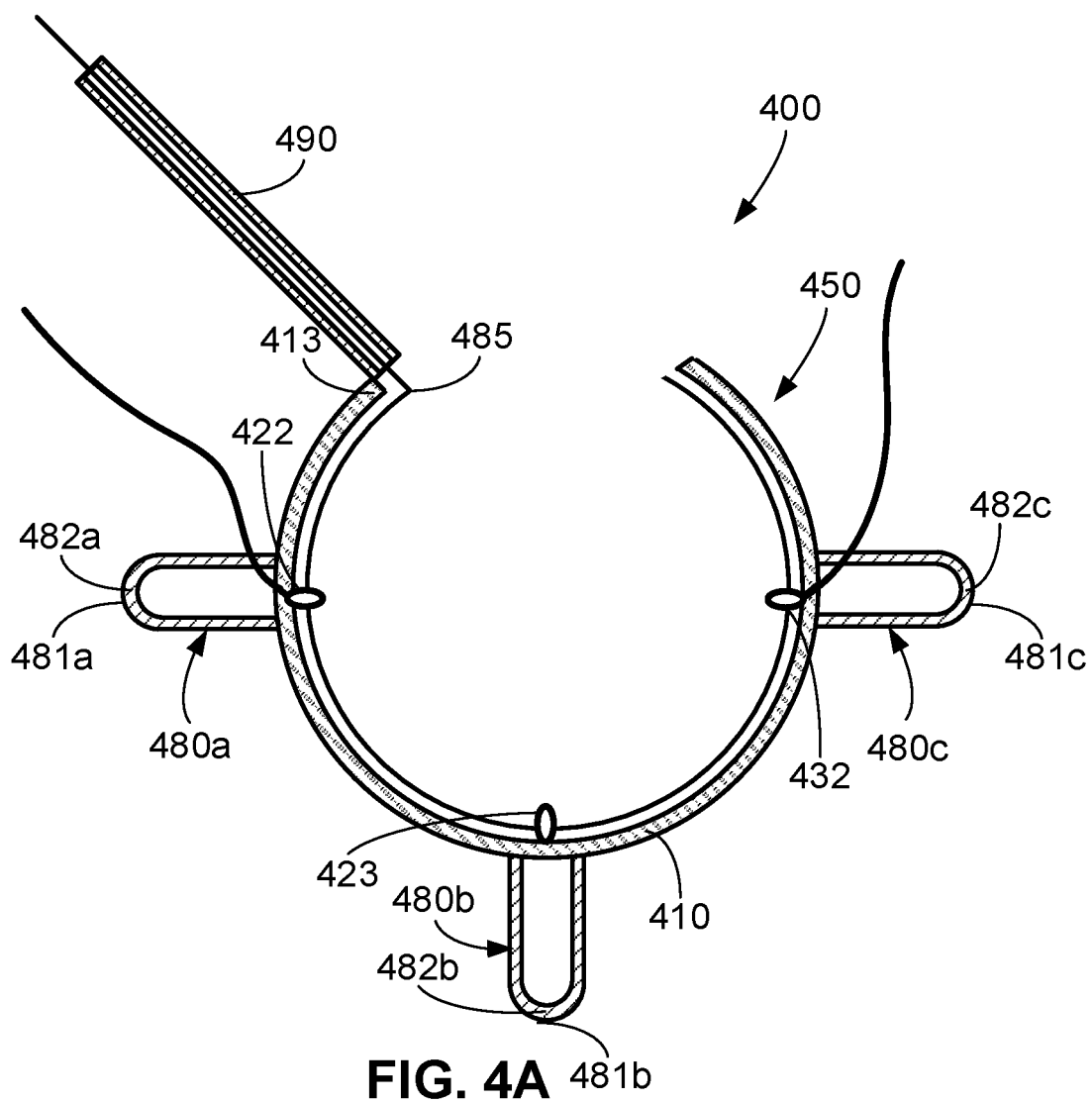
FIG. 4A is a top view of a further example of a tissue anchor system in a deployed state.
Figure 4B:
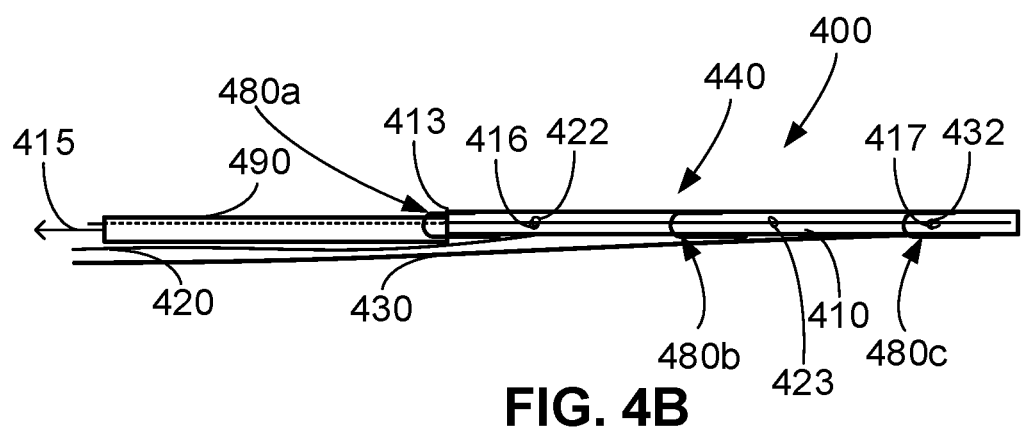
FIGS. 4B-4C are side and top views, respectively, of the tissue anchor system of FIG. 4A in a collapsed state.

FIGS. 4A-4B illustrate another example of a tissue anchor 400 including a central body 410, control members 420, 430, and tissue stabilizing arms 480a, 480b, 480c. The tissue anchor 400 and its components (including the central body 410, the control members 420, 430, and the tissue stabilizing arms 480a, 480b, 480c) can be similar in function and structure to the tissue anchor 300 and its components with some exceptions.

The tissue stabilizing arms 480a, 480b, 480c can extend along radial axes that are perpendicular to one another. For example, the tissue stabilizing arm 480a can extend along a radial axis perpendicular to a radial axis along which the tissue stabilizing arm 480b extends, and the tissue stabilizing arms 480b can extend along a radial axis perpendicular to a radial axis along which the tissue stabilizing arm 480c extends.

The central body 410 and the tissue stabilizing arms 480a, 480b, 480c can be formed of the same material, e.g., a shape memory material, as the central body 310 and the tissue stabilizing arms 380a, 380b, 380c. The central body 410 and the tissue stabilizing arms 480a, 480b, 480c can differ from the central body 310 and the tissue stabilizing arms 380a, 380b, 380c of the tissue anchor 300 in that the central body 410 and the tissue stabilizing arms 480a, 480b, 480c can be formed of a wire structure to reduce an amount of material used to form the tissue anchor 400 and reduce a size of the tissue anchor 400. The tissue stabilizing arms 480a, 480b, 480c can each be formed of a continuous piece of wire that is attached to the central body 410 at two locations. The wires used to form the tissue stabilizing arms 480a, 480b, 480c provide distal tips 481a, 481b, 481c and tissue contact surfaces 482a, 482b, 482c of the tissue anchor 400.

In addition to including the control members 420, 430 (similar to the control members 320, 330 of the tissue anchor 300), the tissue anchor 400 further includes a locking device 485 and a retrieval member 490. The retrieval member 490 is a hollow, tubular member attached to the central body 410 at a first lengthwise end 413 of the central body 410. The retrieval member 490 can be formed of the same material as the central body 410 and the tissue stabilizing arms 480a, 480b, 480c and can be integrally formed with these same components.

The retrieval member 490 can have a circular or elliptical cross-sectional shape. In implementation, a length of the retrieval member 490 can be between 10 and 50 centimeters, e.g., between 10 and 30 centimeters, 20 and 40 centimeters, 30 and 50 centimeters, etc. A width or outer diameter of the retrieval member 490 can be between 0.1 and 1 millimeters, e.g., between 0.1 and 0.7 millimeter, 0.2 and 0.8 millimeters, 0.3 and 0.9 millimeters, 0.4 and 1.0 millimeters, 19 and 26 gauge, no more than 1 millimeter, no less than 19 gauge, etc.

The locking device 485 is an elongate piece of material that extends through the retrieval member 490 and along the central body 410. The locking device 485 can similarly be formed of a shape memory material (e.g., the same shape memory material described for the central body 410). The locking device 485 may be in contact with the central body 410 and is movable relative to the central body 410 and relative to the control members 420, 430. The locking device 485 can be used to attach the control members 420, 430 to the central body 410. For example, the central body 410 can include holes 416, 417 through which loops 422, 432 on the control members 420, 430 extend. The locking device 485 extends through the loops 422, 432 on the control members 420, 430, thereby locking the control members 420, 430 to the central body 410 and preventing the control members 420, 430 from being detached from the central body 410. After the locking device 485 is removed from the central body 410, the loops 422, 432 can be pulled through the holes 416, 417 on the central body 410, thereby allowing the control members 420, 430 to be removed from the central body 410. In some implementations, a loop 423 can be positioned along the central body 410, and the locking device 485 can extend through the loop 423. The locking device 485 can have a diameter sufficiently small to fit within an inner diameter of the retrieval member 490. For example, the locking device 485 can have an outer width or diameter between 0.1 and 0.5 millimeters, e.g., between 0.1 and 0.4 millimeters, 0.2 and 0.5 millimeters, 0.3 and 0.5 millimeters, 26 and 30 gauge, no more than 0.45 millimeters, no less than 26 gauge, etc.

Figure 4C:
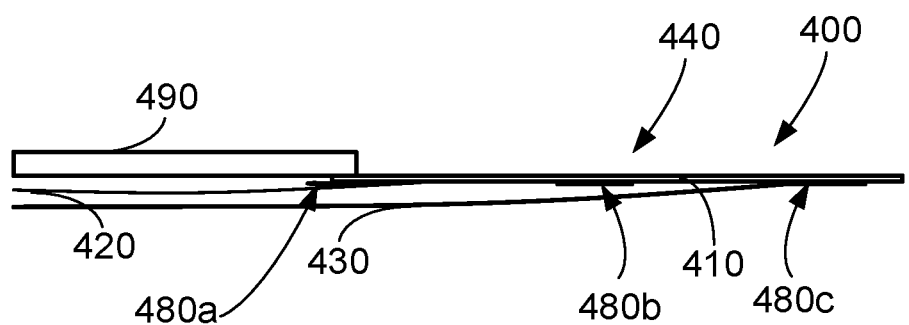

FIGS. 4B-4C illustrate the tissue anchor 400 in the collapsed state 440 in which the central body 410 is straightened out to extend substantially along an axis and the tissue stabilizing arms 480a, 480b, 480c are deformed to extend substantially along the axis. The tissue anchor 400 can be placed in the collapsed state 440, for example, in response to an external force provided by a sheath being placed over the tissue anchor 400 as described in greater detail in this disclosure. In a collapsed state 440 of the tissue anchor 400, the central body 410, the tissue stabilizing arms 380a, 380b, 380c, the retrieval member 490, and the locking device 485 extend along an axis 415.

FIG. 4A illustrates the tissue anchor 400 in the deployed state 450 in which the central body 410 and the tissue stabilizing arms 480a, 480b, 480c is in their neutral states. In a deployed state 450 of the tissue anchor 400, the central body 410 extends along a plane (e.g., corresponding to the plane of the view of FIG. 4A). Although FIG. 4A schematically illustrates the retrieval member 490 as extending in the plane of the view of FIG. 4A, in implementations, in the deployed state 450, the retrieval member 490 protrudes along an axis perpendicular to the plane.

Example Processes of Using Tissue Anchors

Processes using tissue anchors described in this disclosure can include a number of steps and operations. FIGS. 5A-5F, 6A-6F, and 7A-7J illustrate examples of processes that include different steps and operations. The steps and operations performed with respect to these processes can be performed by one or more operators (e.g., a surgeon, a medical practitioner, a nurse, or other medical operator).

FIGS. 5A-5F illustrate a first example of a process including steps 501-505 for delivering and retrieving a tissue anchor 550 through an access location 540 into an anatomical cavity 552. In implementations, the tissue anchor 550 can correspond to the tissue anchor 200 shown in FIGS. 2A-2C and can thus have a configuration similar to that discussed above with respect to the tissue anchor 200. The steps 501-505 can occur sequentially, e.g., with the step 502 being performed after the step 501, the step 503 being performed after the step 502, the step 504 being performed after the step 503, and the step 505 being performed after the step 504.

Figure 5A:
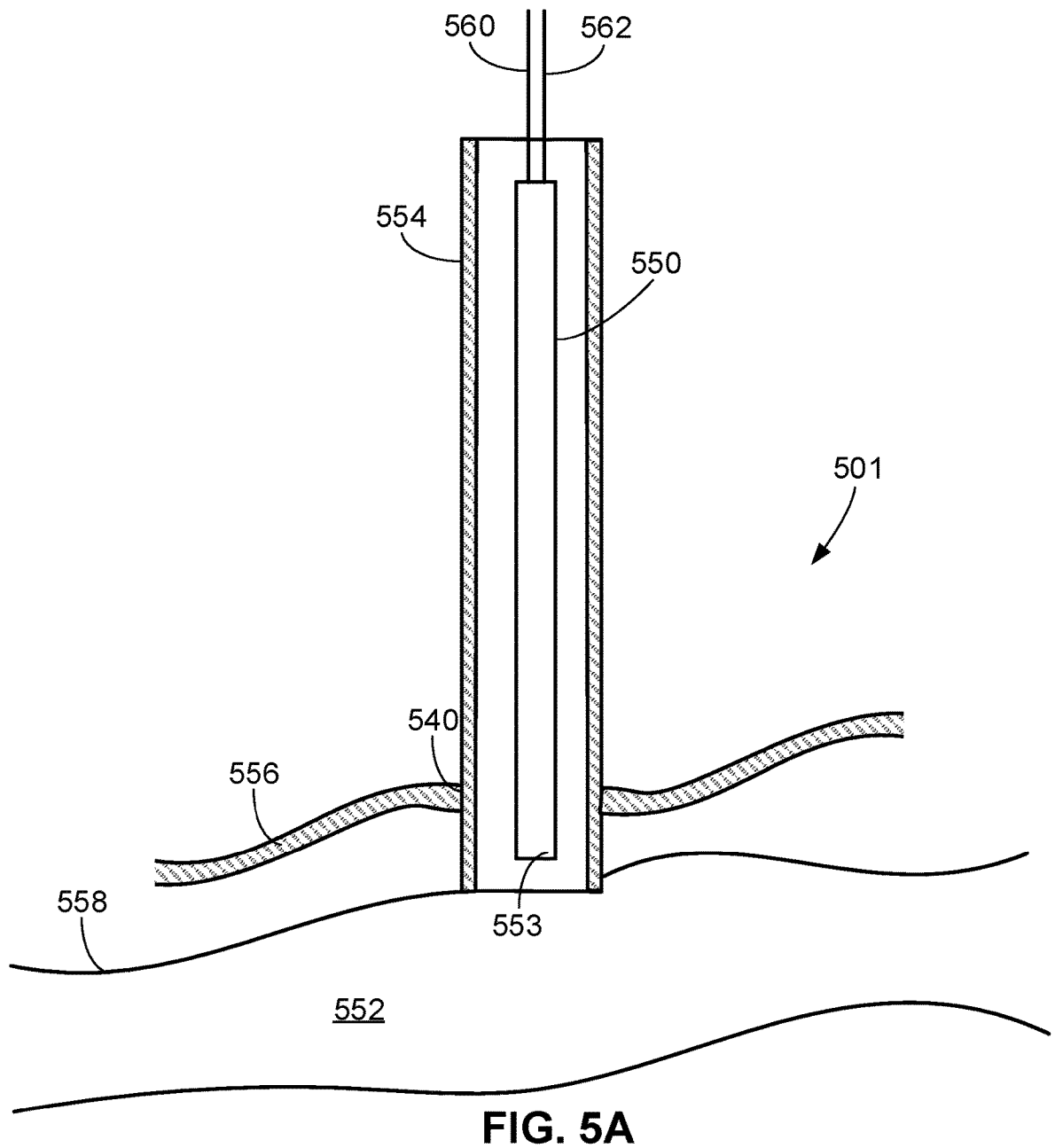
FIGS. 5A-5F illustrate an example of a process for using a tissue anchor system for stabilizing tissue.
Figure 5B:
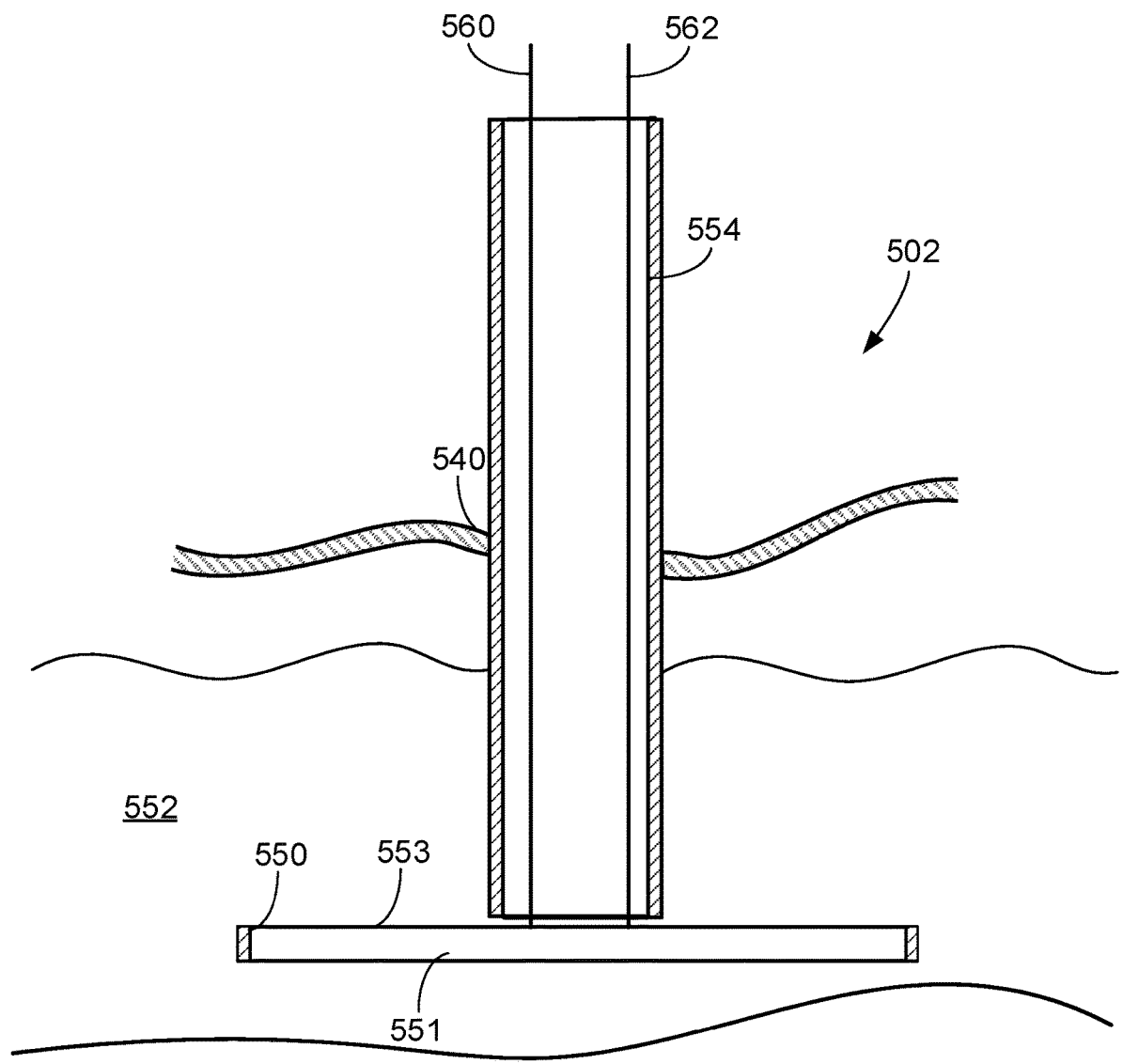

FIGS. 5A-5B illustrate the steps 501-502 that, when performed, position the tissue anchor 550 in the anatomical cavity 552.

In the step 501 illustrated in FIG. 5A, a delivery device 554 is inserted through a first tissue wall 556 and a second tissue wall 558 of a subject. The first tissue wall 556 can correspond to an abdominal wall of the subject, and the second tissue wall 558 can correspond to a tissue wall of the small intestine of the subject. The delivery device 554 can be a puncture device (e.g., a hollow needle, a trocar, a hollow sheath, or another device to pierce tissue walls of the subject) that creates a puncture through the first tissue wall 556 and the second tissue wall 558 at the access location 540.

The delivery device 554 is configured to receive, in an internal portion of the delivery device 554, the tissue anchor 550 in a collapsed state (e.g., the collapsed state 240 shown in FIG. 2C). In the collapsed state, lengthwise ends of a central body 553 of the tissue anchor 550 (e.g., the lengthwise ends 213, 214 shown in FIG. 2C) extend along a longitudinal or insertion axis of the delivery device 554.

When inserted through the first and second tissue walls 556, 558, the delivery device 554 can carry the tissue anchor 550 into the anatomical cavity 552. Alternatively, the tissue anchor 550 can be inserted through the delivery device 554 after the delivery device 554 is inserted through the first tissue wall 556 and the second tissue wall 558. When the tissue anchor 550 is inserted through the delivery device 554, control members 560, 562 of the tissue anchor 550 are manually accessible from outside of the delivery device 554 by the operator, thus allowing the operator to use the control members 560, 562 to manipulate the tissue anchor 550.

In the step 502 illustrated in FIG. 5B, the tissue anchor 550 is inserted into and positioned within the anatomical cavity 552. To push the tissue anchor 550 through the delivery device 554, a pusher (e.g., a rod) can be used. The tissue anchor 550 is further placed in a deployed state (e.g., the deployed state 250 shown in FIGS. 2A-2B) in which the tissue anchor 550 forms an opening 551 through which a medical instrument 542 (shown in FIG. 5D) can be inserted. When in the deployed state, the tissue anchor 550 can have a configuration similar to that shown for the tissue anchor 200 in FIGS. 2A-2B.

To transition from the collapsed state to the deployed state, the tissue anchor 550 can be configured to have a neutral state corresponding to the deployed state. For example, as discussed with respect to the tissue anchor 200 of FIGS. 2A-2C, the central body 553 of the tissue anchor 550 can be formed of a shape memory material that biases the tissue anchor 550 toward the deployed state when the tissue anchor 550 is in the collapsed state. As the tissue anchor 550 is inserted beyond the delivery device 554 into the anatomical cavity 552 and the delivery device 554 no longer surrounds the tissue anchor 550 and no longer applies forces on the tissue anchor 550, the tissue anchor 550 is placed in the deployed state. The tissue anchor 550 and, in particular, the central body 553 of the tissue anchor 550 expands radially outwardly to a configuration similar to that shown in FIGS. 2A-2B, thereby causing the tissue anchor 550 to form the opening 551.

As the tissue anchor 550 is inserted into the anatomical cavity 552, at least some portions of the control members 560, 562 are maintained outside of the anatomy so that the operator can manually access the control members 560, 562.

In some implementations, a dilator, a balloon, or a stent is inserted through the delivery device 554 and then into the opening 551 of the tissue anchor 550 to enlarge a size of the opening 551 of the tissue anchor 550. The desired diameter can be selected based on, for example, a desired size of a workspace within the anatomical cavity 552 or a size of the medical instrument 542 to be used.

Figure 5C:
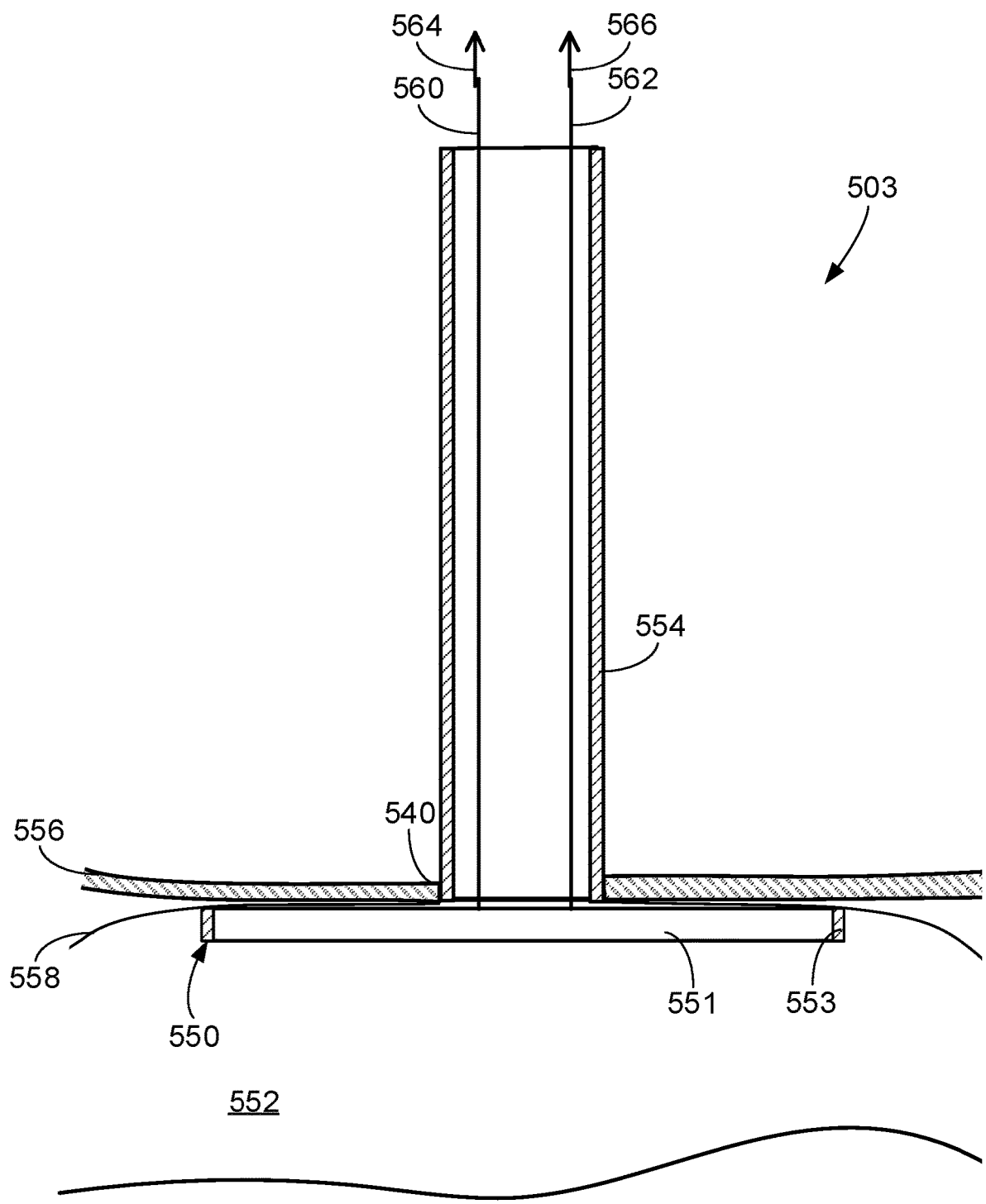
Figure 5D:
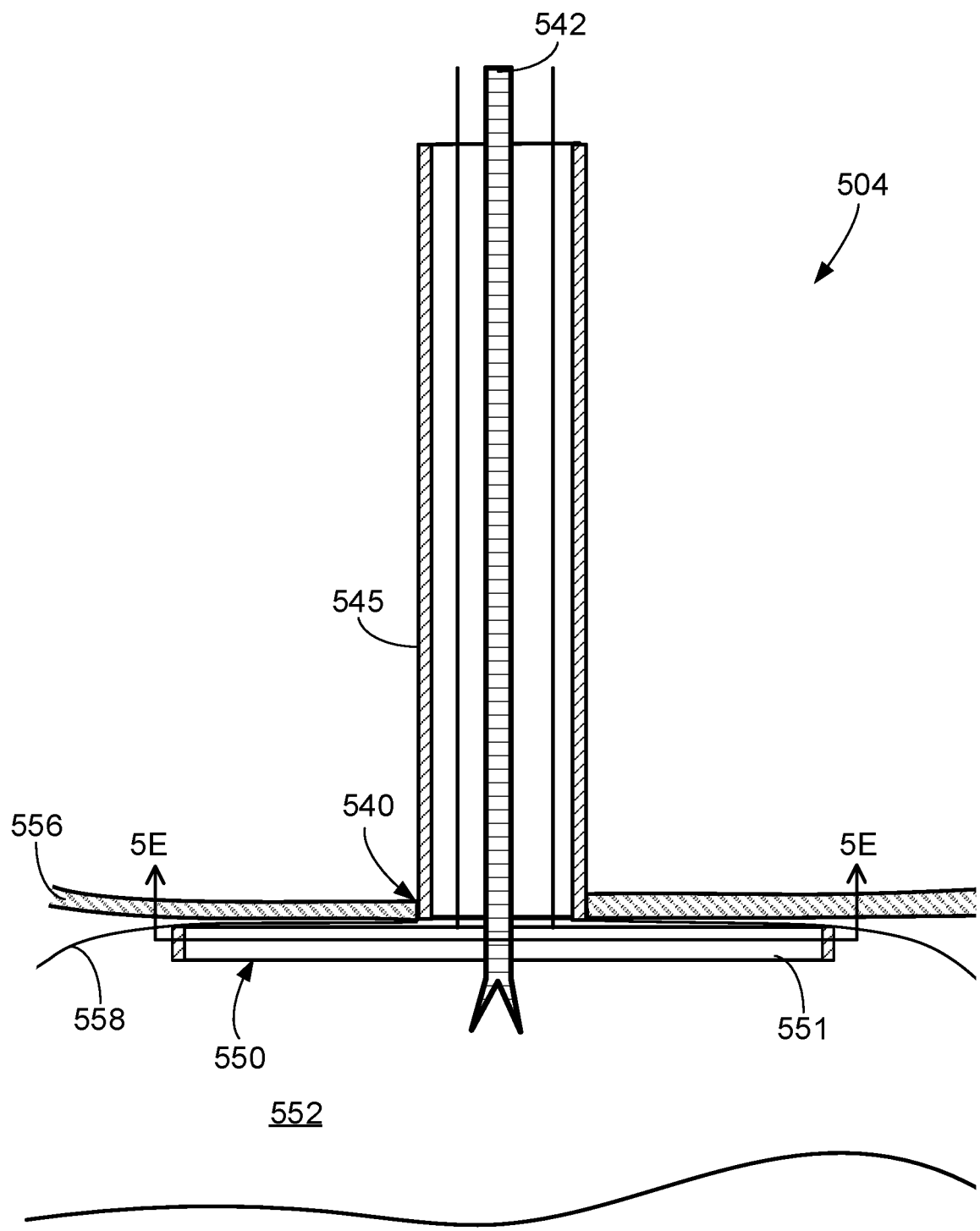
Figure 5E:
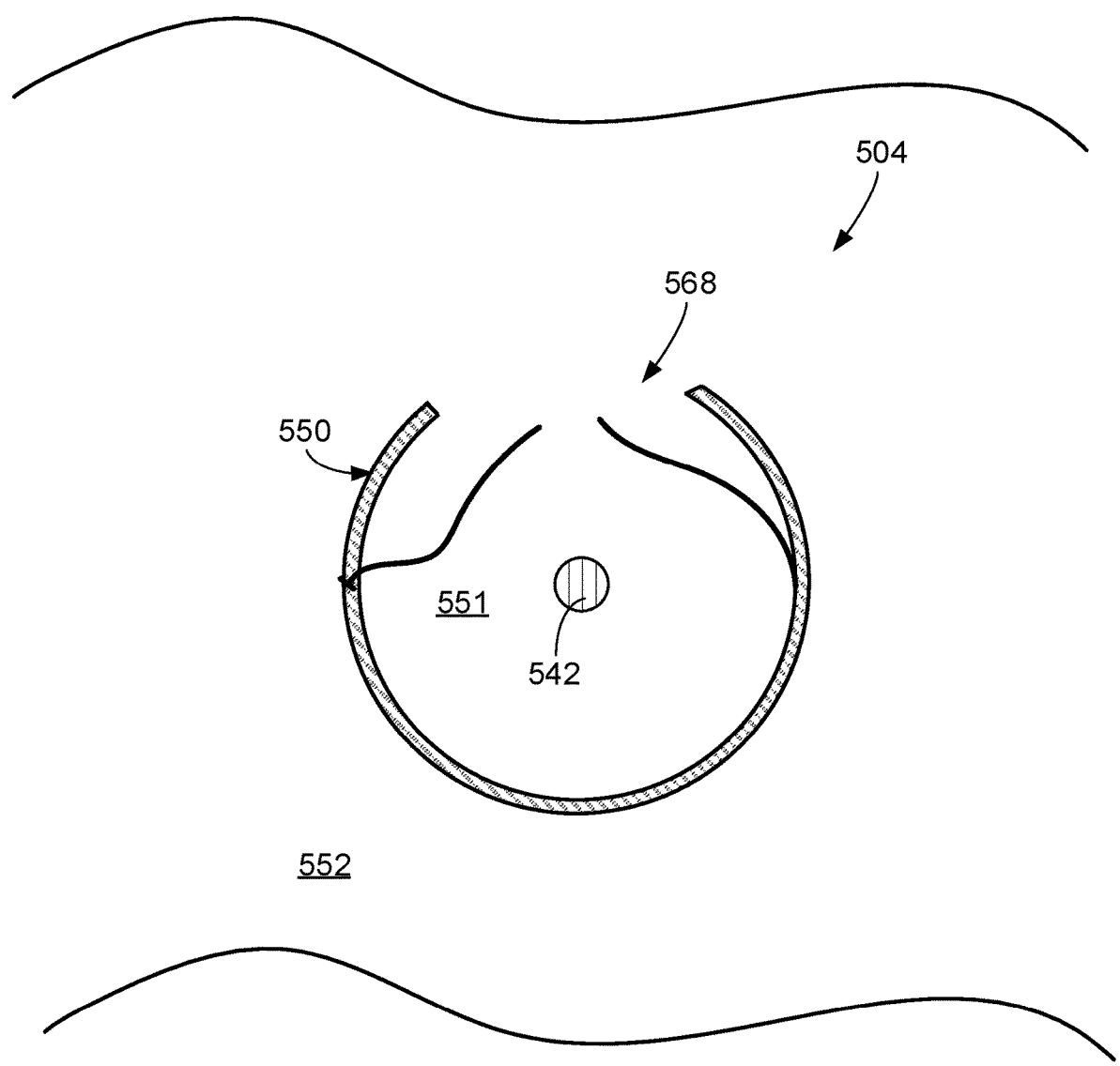

FIGS. 5C-5E illustrate steps 503-504 that correspond to steps in which the tissue anchor 550 is in engagement with the second tissue wall 558 in the deployed state of the tissue anchor 550.

In the step 503 illustrated in FIG. 5C, the tissue anchor 550 in the deployed state is caused to engage with the second tissue wall 558 to stabilize the second tissue wall 558. One or more pulling forces (e.g., pulling forces 564, 566) are applied to the tissue anchor 550 (e.g., in a direction away from the anatomical cavity 552). The central body 553 is pulled into contact with the second tissue wall 558 with the pulling forces 564, 566, and the second tissue wall 558 is pulled toward the first tissue wall 556.

The tissue anchor 550 is pulled using one or more of the control members 560, 562. The control member 560, by being attached to a first lengthwise half of the central body 553 of the tissue anchor 550 (e.g., the first lengthwise half 211 shown in FIGS. 2A-2C), allows the pulling force 564 to be applied to the first lengthwise half of the central body 553 of the tissue anchor 550. And the control member 562, by being attached to a second lengthwise half of the central body 553 of the tissue anchor 550 (e.g., the second lengthwise half 212 shown in FIGS. 2A-2C), allows the pulling force 566 to be applied to the second lengthwise half of the central body 553 of the tissue anchor 550. Pulling the second tissue wall 558 toward the first tissue wall 556 can cause a portion of the second tissue wall 558 to be pulled taut. In addition, although the delivery device 554 is depicted as being positioned at the access location 540 during the step 503, in some implementations, the delivery device 554 is removed after the tissue anchor 550 is positioned in the anatomical cavity 552, after the tissue anchor 550 is in the deployed state, and/or after the tissue anchor 550 is engaged with the second tissue wall 558.

FIGS. 5D-5E illustrate a step 504 for delivery of the medical instrument 542 into the anatomical cavity 552, with FIG. 5D showing a side sectional view and FIG. 5E showing a cross-sectional view along the section line 5E-5E shown in FIG. 5D. In the step 504 illustrated in FIGS. 5D and 5E, the tissue anchor 550 in the deployed state is maintained in engagement with the second tissue wall 558, and at least a portion of the medical instrument 542 is delivered into the anatomical cavity 552 with the medical instrument 542 aligned with the opening 551 of the tissue anchor 550. In some implementations, an instrument sheath 545 in inserted through the access location 540 and through the first and second tissue walls 556, 558 before the medical instrument 542 is placed into the anatomical cavity 552. The portion of the medical instrument 542 is, for example, inserted through the opening 551 of the tissue anchor 550 while the tissue anchor 550 is engaged with the second tissue wall 558. This engagement between the tissue anchor 550 and the second tissue wall 558 can improve the stability of the second tissue wall 558, thereby making it easier to deliver the portion of the medical instrument 542 into the anatomical cavity 552. As shown in FIG. 5E, the portion of the medical instrument 542 is surrounded by the tissue anchor 550 and a slot 568 defined by the tissue anchor 550.

Figure 5F:
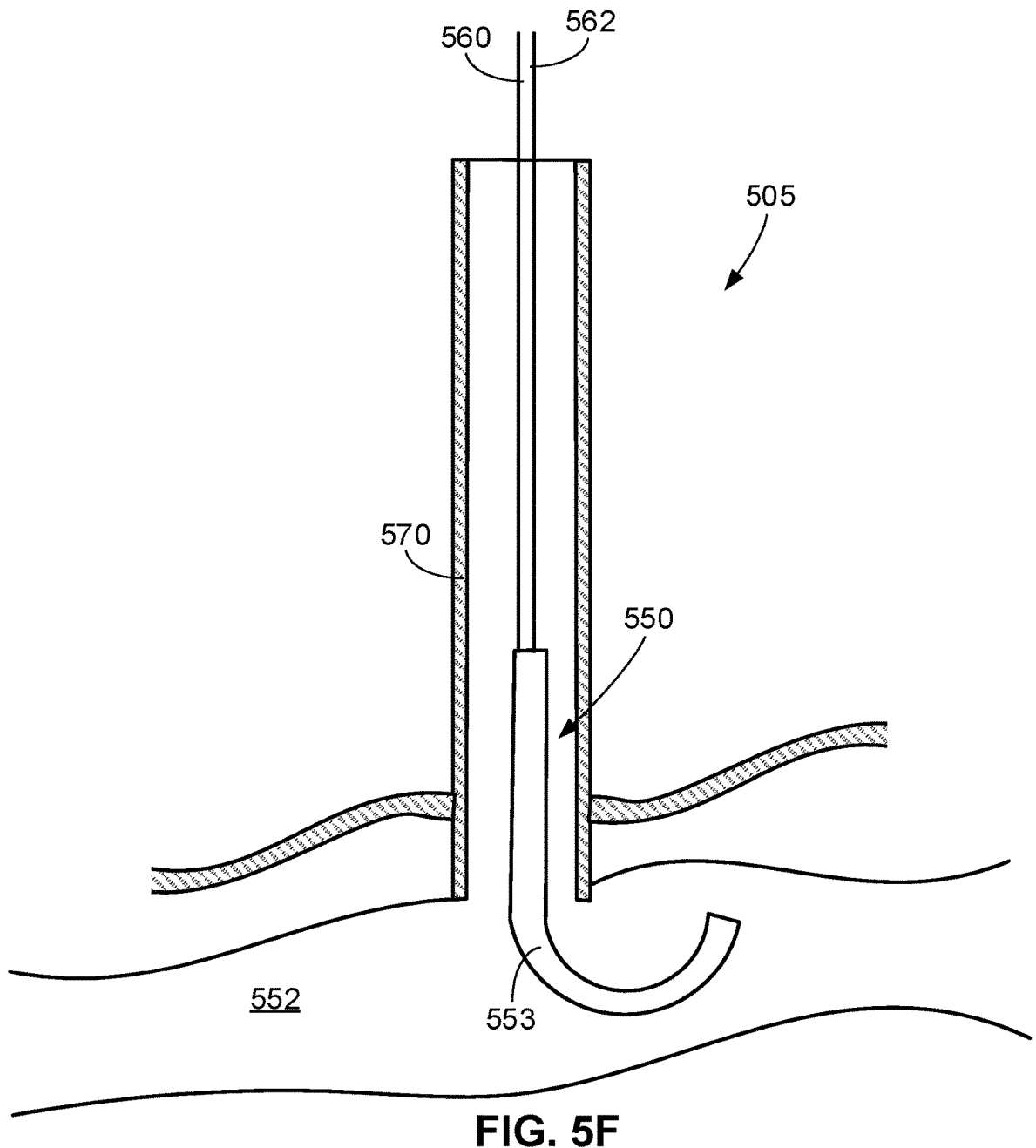

FIG. 5F illustrates a step 505 for withdrawing the tissue anchor 550 from the anatomical cavity 552. In the step 505 illustrated in FIG. 5F, the tissue anchor 550 is withdrawn from the anatomical cavity 552. Before being withdrawn from the anatomical cavity 552, the one or more pulling forces on the tissue anchor 550 are released. Then, the tissue anchor 550 is placed in the collapsed state (e.g., the collapsed state 240 shown in FIG. 2C) in a retrieval sheath 570. In this transition to the collapsed state, the first lengthwise end and the second lengthwise end of the central body 553 of the tissue anchor 550 move away from one another, thereby causing the central body 553 to form a straightened structure positionable in the retrieval sheath 570. The walls of the retrieval sheath 570 can apply a force on the tissue anchor 550 as the tissue anchor 550 is pulled into the retrieval sheath 570, e.g., using the control members 560, 562. This force causes the tissue anchor 550 to transition from the deployed state (FIGS. 2A-2B) to the collapsed state (FIG. 2C). The tissue anchor 550 can be withdrawn by pulling the control members 560, 562, advancing the retrieval sheath 570 toward the anatomical cavity 552 relative to the tissue anchor 550, or a combination of both pulling the control members 560, 562 and advancing the retrieval sheath 570.

FIGS. 6A-6F illustrates a second example of a process including steps 601-605 for delivering and retrieving a tissue anchor 650 through an access location 640 into an anatomical cavity 652. In implementations, the tissue anchor 650 can correspond to the tissue anchor 300 shown in FIGS. 3A-3D and can thus have a configuration similar to that discussed above with respect to the tissue anchor 300. The steps 601-605 can occur sequentially, e.g., with the step 602 being performed after the step 601, the step 603 being performed after the step 602, the step 604 being performed after the step 603, and the step 605 being performed after the step 604.

The process illustrated in FIGS. 6A-6F is identical to the process illustrated in FIGS. 5A-5F with the primary exception that the process in FIGS. 6A-6F involves a tissue anchor 650 that includes tissue stabilizing arms 680a, 680b, 680c. Specifically, the process of FIGS. 6A-6F uses a tissue anchor 650 similar to the tissue anchor 300 of FIGS. 3A-3D, while the process of FIGS. 5A-5F uses a tissue anchor 550 similar to the tissue anchor 200 of FIGS.

Figure 6A:
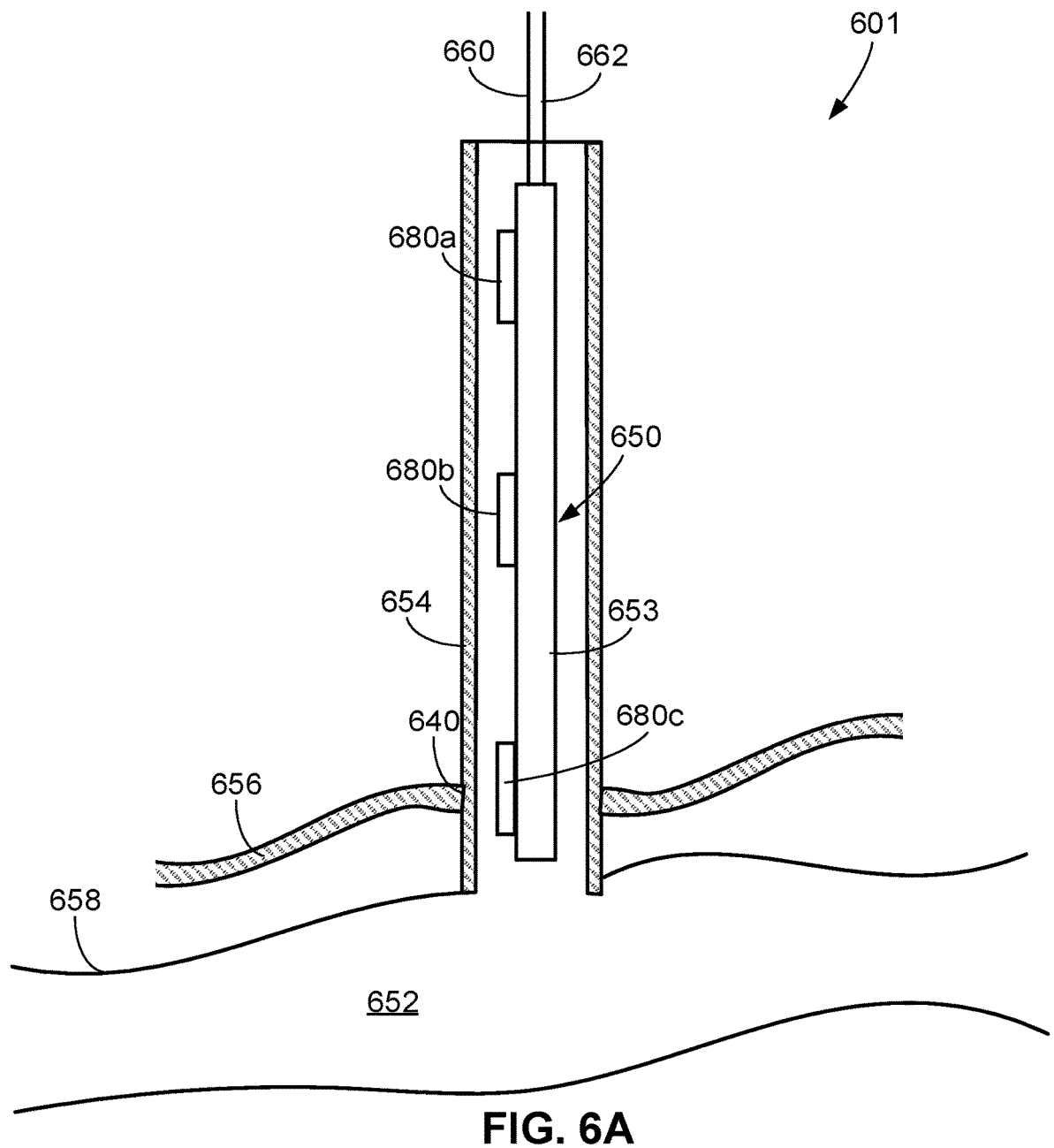
FIGS. 6A-6F illustrate another example of a process for using a tissue anchor system for stabilizing tissue in anatomy of a subject.
Figure 6B:
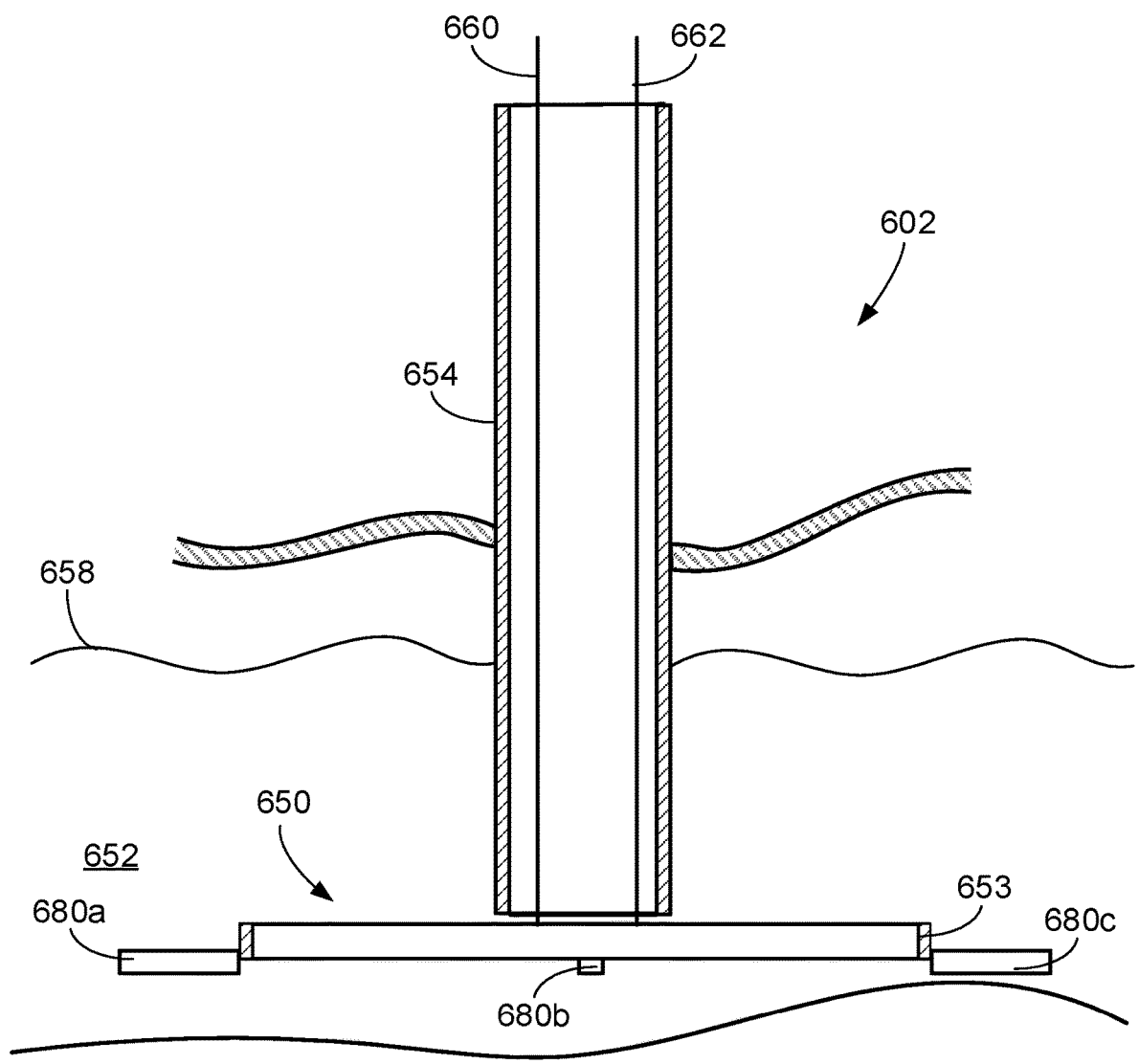

FIGS. 6A-6B illustrate steps 601-602 that, when performed, position the tissue anchor 650 in the anatomical cavity 652.

In the step 601 illustrated in FIG. 6A, a delivery device 654 (e.g., similar to the delivery device 554) is inserted through a first tissue wall 656 and the second tissue wall 658 of a subject. The first tissue wall 656 can correspond to an abdominal wall of the subject, and the second tissue wall 658 can correspond to a tissue wall of the small intestine of the subject. The delivery device 654 can be a puncture device (e.g., a hollow needle, a trocar, a hollow sheath, or another device to pierce tissue walls of the subject) that creates a puncture through the first tissue wall 656 and the second tissue wall 658 at the access location 640.

The delivery device 654 is configured to receive, in an internal portion of the delivery device 654, the tissue anchor 650 in a collapsed state (e.g., the collapsed state 340 shown in FIG. 3C). In the collapsed state, lengthwise ends of a central body 653 of the tissue anchor 650 (e.g., the lengthwise ends shown in FIG. 3C) and the tissue stabilizing arms 680a, 680b, 680c (e.g., the tissue stabilizing arms 380a, 380b, 380c in FIG. 3C) extend along a longitudinal or insertion axis of the delivery device 654.

When inserted through the first and second tissue walls 656, 658, the delivery device 654 can carry the tissue anchor 650 into the anatomical cavity 652. Alternatively, the tissue anchor 650 can be inserted through the delivery device 654 after the delivery device 654 is inserted through the first tissue wall 656 and the second tissue wall 658. When the tissue anchor 650 is inserted through the delivery device 654, control members 660, 662 of the tissue anchor 650 are manually accessible from outside of the delivery device 654 by the operator, thus allowing the operator to use the control members 660, 662 to manipulate the tissue anchor 650.

In the step 602 illustrated in FIG. 6B, the tissue anchor 650 is inserted into and positioned within the anatomical cavity 652. To push the tissue anchor 650 through the delivery device 654, a pusher (e.g., a rod) can be used. The tissue anchor 650 is further placed in a deployed state (e.g., the deployed state 350 shown in FIGS. 3A-3B) in which the tissue anchor 650 forms an opening 651 through which a medical instrument 642 (shown in FIG. 6D) can be inserted. In some implementations, an instrument sheath 645 in inserted through the access location 640 and through the first and second tissue walls 656, 658 before the medical instrument 642 is placed into the anatomical cavity 652. When in the deployed state, the tissue anchor 650 can have a configuration similar to that shown for the tissue anchor 300 in FIGS.

To transition from the collapsed state to the deployed state, the tissue anchor 650 can be configured to have a neutral state corresponding to the deployed state. For example, as discussed with respect to the tissue anchor 300 of FIGS. 3A-3D, the central body 653 and the tissue stabilizing arms 680a, 680b, 680c of the tissue anchor 650 can be formed of a shape memory material that biases the tissue anchor 650 toward the deployed state when the tissue anchor 650 is in the collapsed state. As the tissue anchor 650 is inserted beyond the delivery device 654 into the anatomical cavity 652 and the delivery device 654 no longer surrounds the tissue anchor 650 and no longer applies forces on the tissue anchor 650, the tissue anchor 650 is placed in the deployed state. The central body 653 and the tissue stabilizing arms 680a, 680b, 680c of the tissue anchor 650 expand radially outwardly to a configuration similar to that shown in FIGS. 3A-3B, thereby causing the tissue anchor 650 to form the opening 651 and causing the tissue stabilizing arms 680a, 680b, 680c to be in position to contact the second tissue wall 658. The tissue stabilizing arms 680a, 680b, 680c extend outwardly in response to the tissue anchor 650 being moved beyond the delivery device 654 and into the anatomical cavity 652, thus removing forces applied to the tissue anchor 650 by the internal walls of the delivery device 654.

As the tissue anchor 650 is inserted into the anatomical cavity 652, at least some portions of the control members 660, 662 are maintained outside of the anatomy so that the operator can manually access the control members 660, 662.

In some implementations, a dilator, a balloon, or a stent is inserted through the delivery device 654 and then into the opening 651 of the tissue anchor 650 to enlarge a size of the opening 651 of the tissue anchor 650. The desired diameter can be selected based on, for example, a desired size of a workspace within the anatomical cavity 652 or a size of the medical instrument 642 to be used.

Figure 6C:
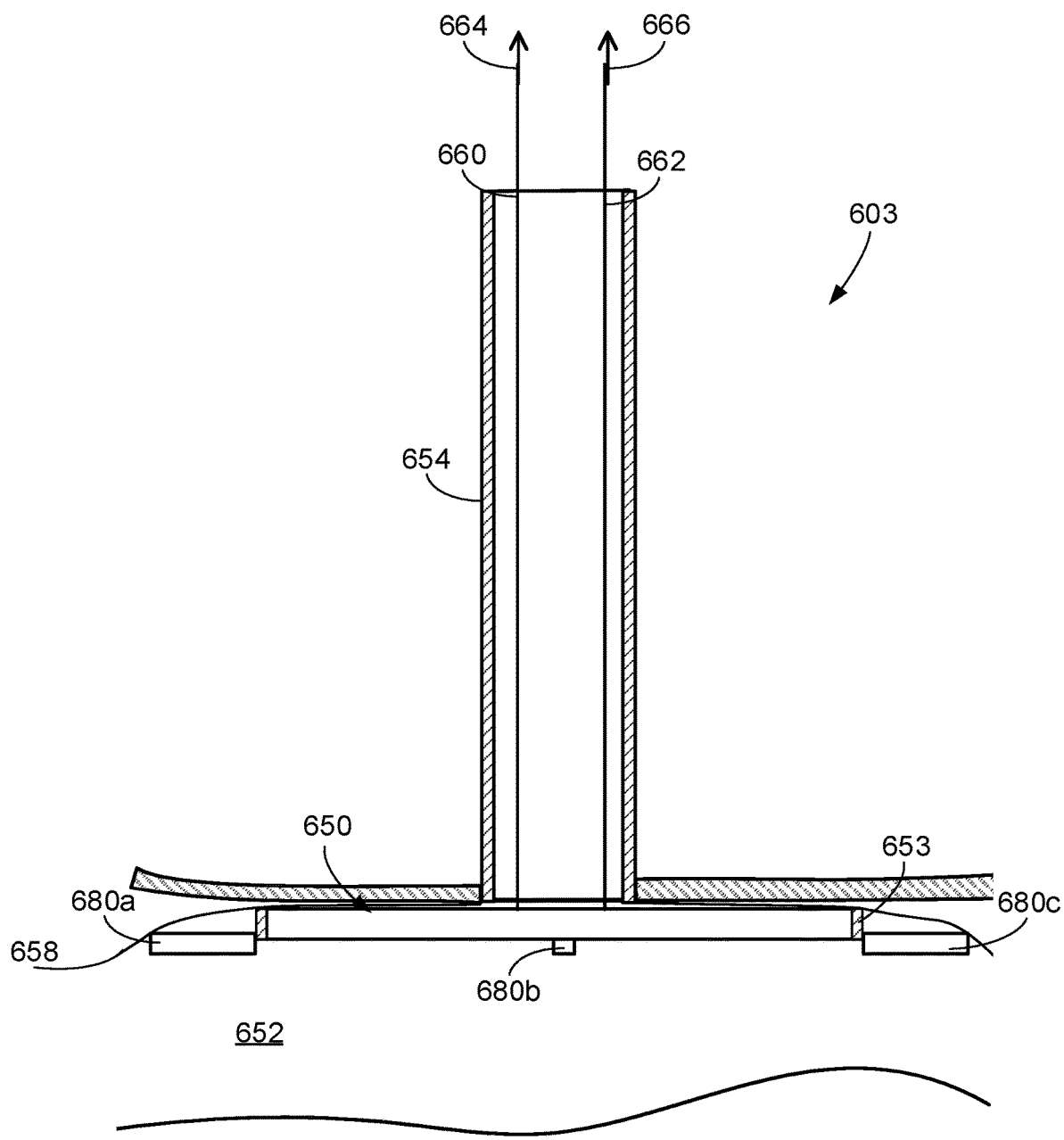
Figure 6D:
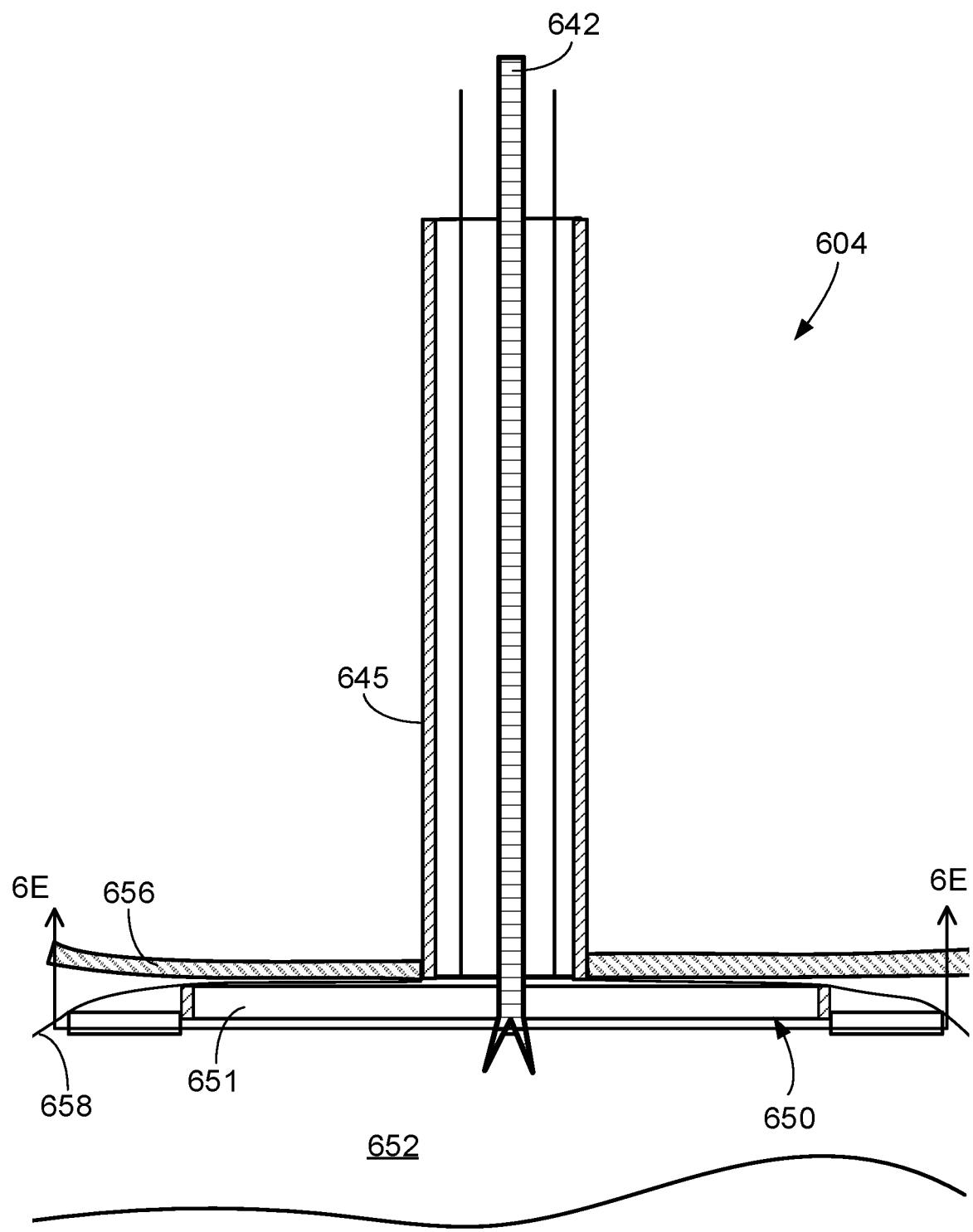
Figure 6E:
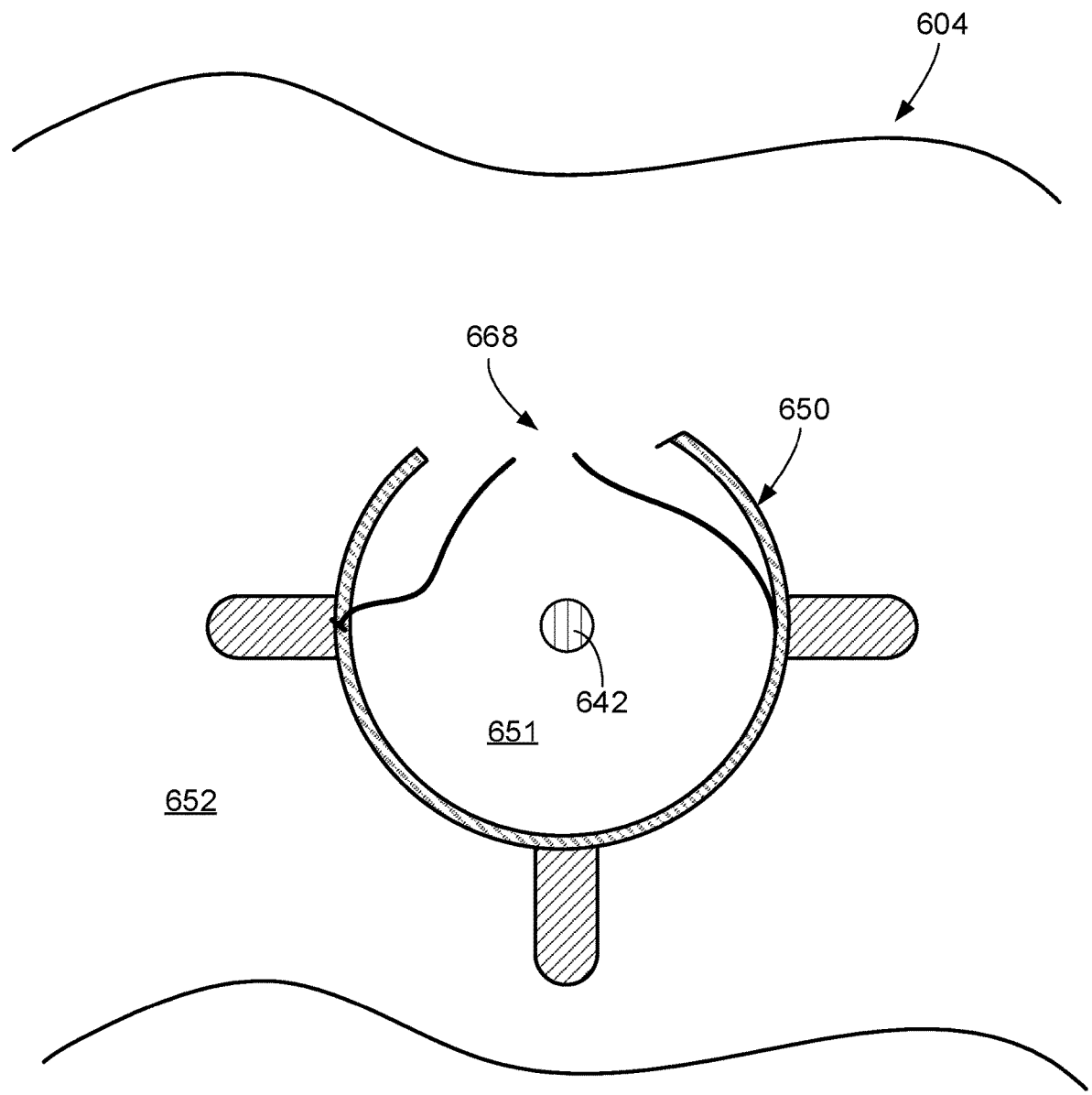

FIGS. 6C-6E illustrate steps 603-604 that correspond to steps in which the tissue anchor 650 is in engagement with the second tissue wall 658 in the deployed state of the tissue anchor 650.

In the step 603 illustrated in FIG. 6C, the tissue anchor 650 in the deployed state is caused to engage with the second tissue wall 658 to stabilize the second tissue wall 658. One or more pulling forces (e.g., pulling forces 664, 666) are applied to the tissue anchor 650 (e.g., in a direction away from the anatomical cavity 652). The central body 653 and the tissue stabilizing arms 680a, 680b, 680c are pulled into contact with the second tissue wall 658 with the pulling forces 664, 666, and the second tissue wall 658 is pulled toward the first tissue wall 656. The tissue contact surfaces of the tissue stabilizing arms 680a, 680b, 680c (e.g., the tissue contact surfaces 382a, 382b, 382c shown in FIGS. 3A-3B) contact the second tissue wall 658.

The tissue anchor 650 is pulled using one or more of the control members 660, 662. The control member 660, by being attached to a first lengthwise half of the central body 653 of the tissue anchor 650 (e.g., the first lengthwise half shown in FIGS. 3A-3D), allows the pulling force 664 to be applied to the first lengthwise half of the central body 653 of the tissue anchor 650. And the control member 662, by being attached to a second lengthwise half of the central body 653 of the tissue anchor 650 (e.g., the first lengthwise half shown in FIGS. 3A-3D), allows the pulling force 666 to be applied to the second lengthwise half of the central body 653 of the tissue anchor 650. Pulling the second tissue wall 658 toward the first tissue wall 656 can cause a portion of the second tissue wall 658 to be pulled taut. In addition, although the delivery device 654 is depicted as being positioned at the access location 640 during the step 603, in some implementations, the delivery device 654 is removed after the tissue anchor 650 is positioned in the anatomical cavity 652, after the tissue anchor 650 is in the deployed state, and/or after the tissue anchor 650 is engaged with the second tissue wall 658.

FIGS. 6D-6E illustrate a step 604 for delivery of the medical instrument 642 into the anatomical cavity 652, with FIG. 6D showing a side sectional view and FIG. 6E showing a cross-sectional view along the section line 6E-5E shown in FIG. 6D. In the step 604 illustrated in FIGS. 6D and 6E, at least a portion of the medical instrument 642 is delivered into the anatomical cavity 652 with the medical instrument 642 aligned with the opening 651 of the tissue anchor 650. The portion of the medical instrument 642 is, for example, inserted through the opening 651 of the tissue anchor 650 while the tissue anchor 650 is engaged with the second tissue wall 658. This engagement between the tissue anchor 650 and the second tissue wall 658 can improve the stability of the second tissue wall 658, thereby making it easier to deliver the portion of the medical instrument 642 into the anatomical cavity 652. As shown in FIG. 6E, the portion of the medical instrument 642 is surrounded by the tissue anchor 650 and a slot 668 defined by the tissue anchor 650.

Figure 6F:
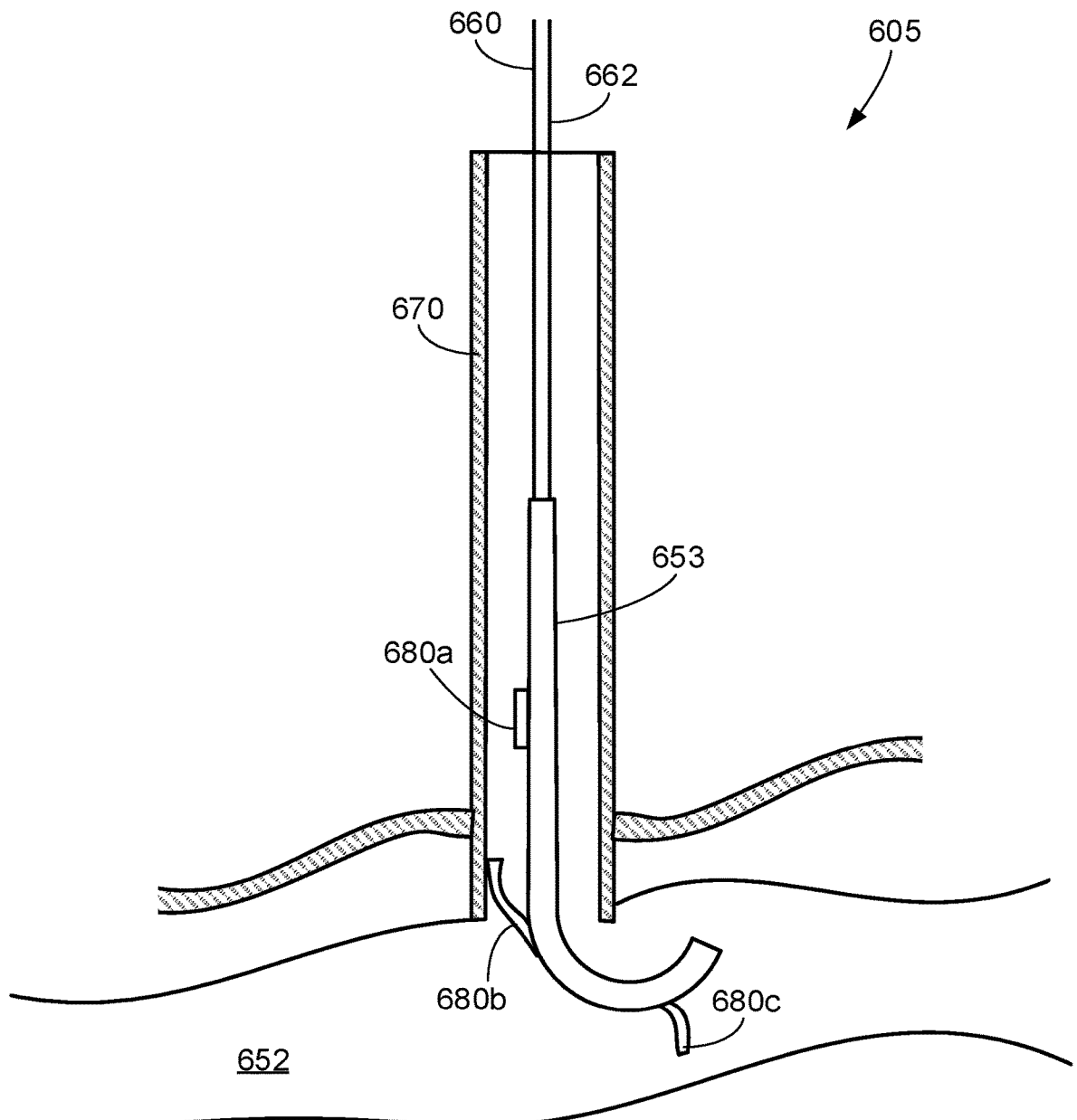

FIG. 6F illustrates a step 605 for withdrawing the tissue anchor 650 from the anatomical cavity 652. In the step 605 illustrated in FIG. 6F, the tissue anchor 650 is withdrawn from the anatomical cavity 652. Before being withdrawn from the anatomical cavity 652, the one or more pulling forces on the tissue anchor 650 are released. Then, the tissue anchor 650 is placed in the collapsed state (e.g., the collapsed state 340 shown in FIG. 3C) in a retrieval sheath 670. In this transition to the collapsed state, the first lengthwise end and the second lengthwise end of the central body 653 of the tissue anchor 650 move away from one another, thereby causing the central body 653 to form a straightened structure positionable in the retrieval sheath 670. The walls of the retrieval sheath 670 can apply a force on the tissue anchor 650 as the tissue anchor 650 is pulled into the retrieval sheath 670, e.g., using the control members 660, 662. This force causes the tissue anchor 650 to transition from the deployed state (FIGS. 3A-3B) to the collapsed state (FIGS. 3C-3D). The tissue anchor 650 can be withdrawn by pulling the control members 660, 662, advancing the retrieval sheath 670 toward the anatomical cavity 652 relative to the tissue anchor 650, or a combination of both pulling the control members 660, 662 and advancing the retrieval sheath 670.

FIGS. 7A-7J illustrate a second example of a process including steps 701-710 for delivering and retrieving a tissue anchor 750 through an access location 740 into an anatomical cavity 752. In implementations, the tissue anchor 750 can correspond to the tissue anchor 400 shown in FIGS. 4A-4C and can thus have a configuration similar to that discussed above with respect to the tissue anchor 400. The tissue anchor 750, for example, includes a central body 753, control members 760, 762, a retrieval member 782, and a locking device 784 similar to those described with respect to the tissue anchor 400. The steps 701-710 can occur sequentially, e.g., with the step 702 being performed after the step 701, the step 703 being performed after the step 702, the step 704 being performed after the step 703, the step 705 being performed after the step 704, the step 706 being performed after the step 705, the step 707 being performed after the step 706, the step 708 being performed after the step 707, the step 709 being performed after the step 708, and the step 710 being performed after the step 709.

Figure 7A:
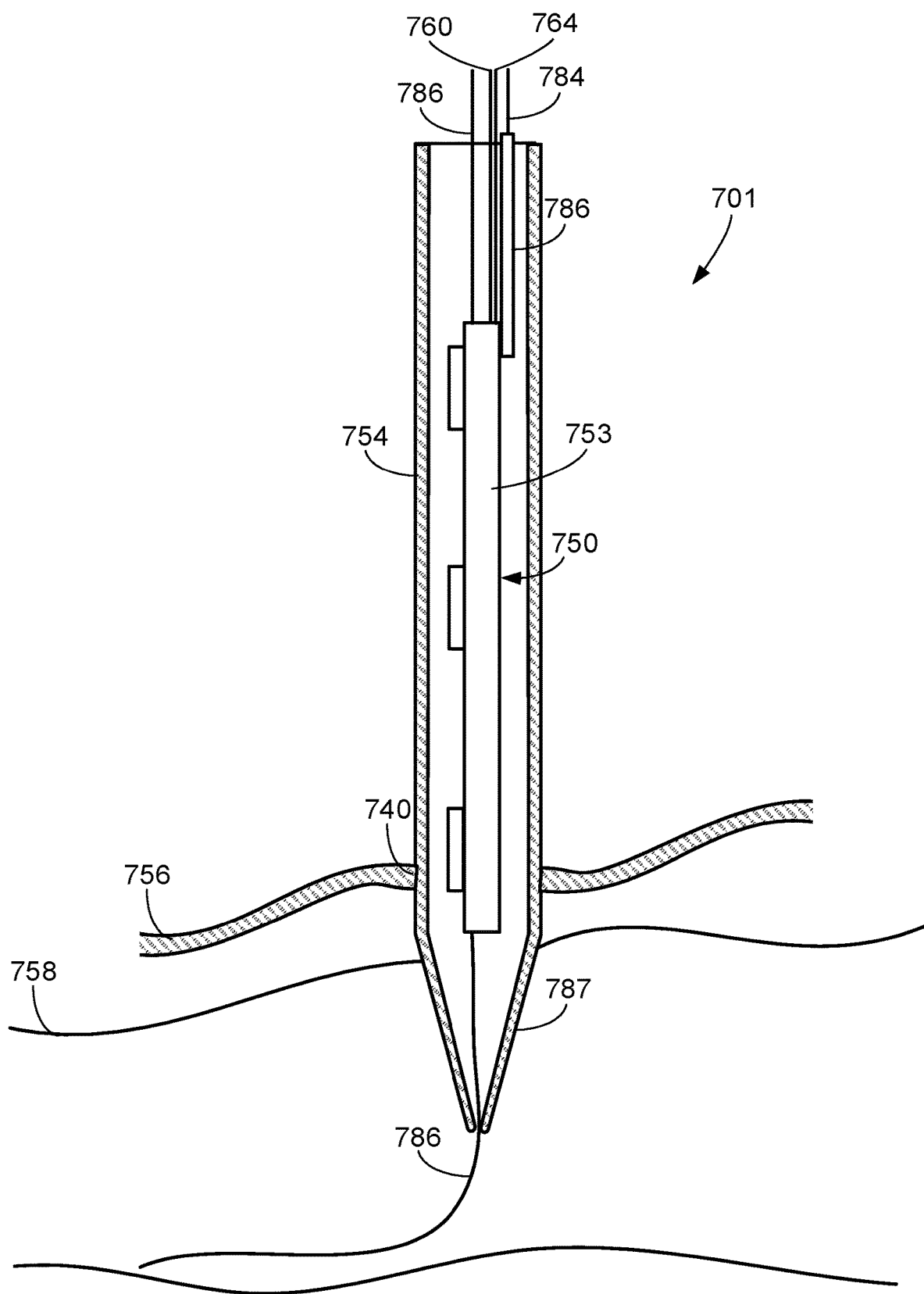
FIGS. 7A-7J illustrate a further example of a process for using a tissue anchor system for stabilizing tissue of an anatomy of a subject.
Figure 7B:
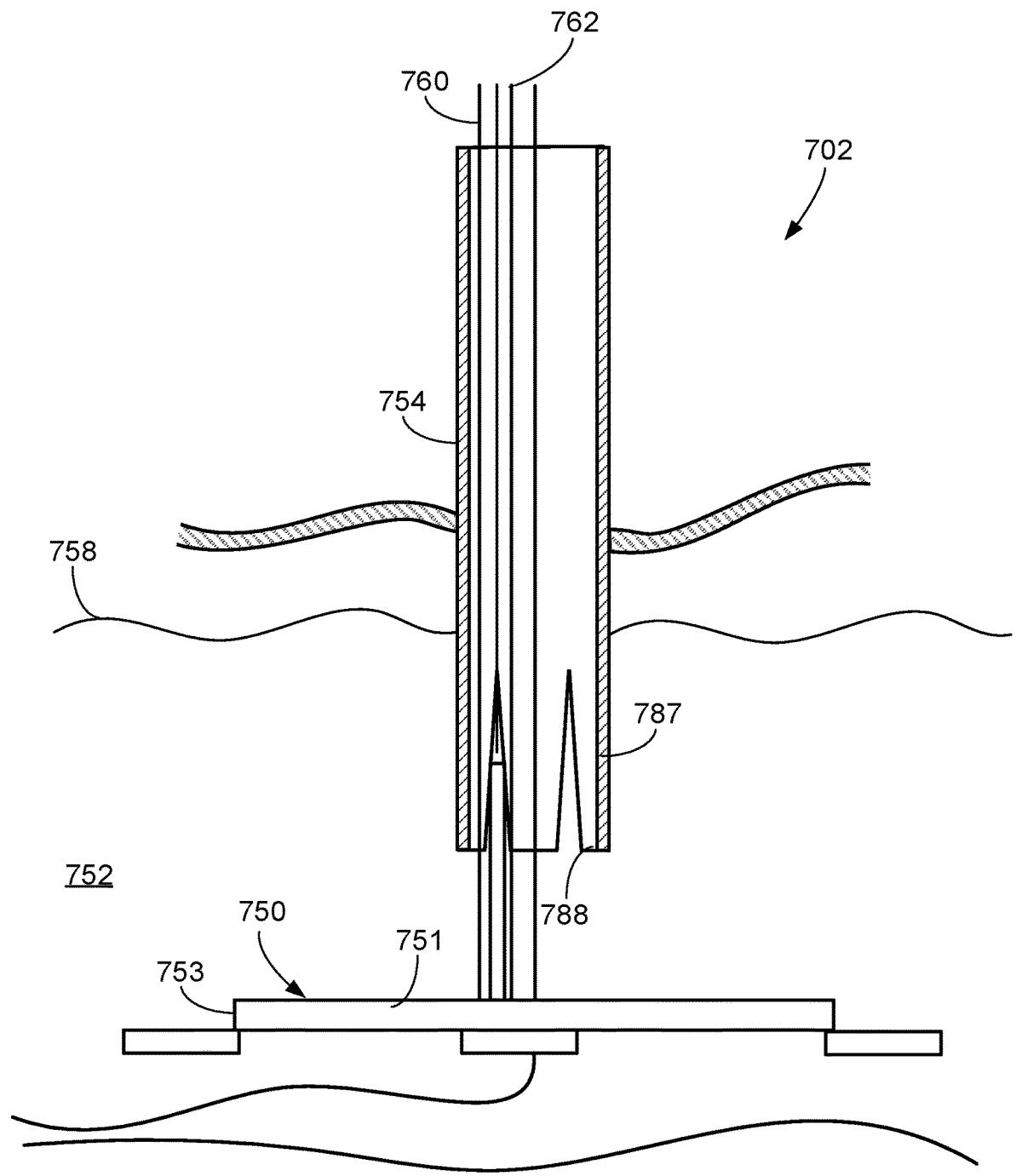

FIGS. 7A-7B illustrate steps 701-702 that, when performed, position the tissue anchor 750 in the anatomical cavity 752.

In the step 701 illustrated in FIG. 7A, a delivery device 754 (e.g., similar to the delivery device 554) is inserted through a first tissue wall 756 and the second tissue wall 758 of a subject. The first tissue wall 756 can correspond to an abdominal wall of the subject, and the second tissue wall 758 can correspond to a tissue wall of the small intestine of the subject. The delivery device 754 can be a puncture device (e.g., a hollow needle, a trocar, a hollow sheath, or another device to pierce tissue walls of the subject) that creates a puncture through the first tissue wall 756 and the second tissue wall 758 at the access location 740.

The delivery device 754 is configured to receive, in an internal portion of the delivery device 754, the tissue anchor 750 in a collapsed state (e.g., the collapsed state 440 shown in FIGS. 4B-4C). In the collapsed state, lengthwise ends of a central body 753 of the tissue anchor 750 (e.g., the lengthwise ends shown in FIGS. 4B-4C), the tissue stabilizing arms 780a, 780b, 780c (e.g., the tissue stabilizing arms 480a, 480b, 480c in FIGS. 4B-4C), and the retrieval member 782 extend along a longitudinal or insertion axis of the delivery device 754.

When inserted through the first and second tissue walls 756, 758, the delivery device 754 can carry the tissue anchor 750 into the anatomical cavity 752. Alternatively, the tissue anchor 750 can be inserted through the delivery device 754 after the delivery device 754 is inserted through the first tissue wall 756 and the second tissue wall 758. When the tissue anchor 750 is inserted through the delivery device 754, the control members 760, 762 and the locking device 784 of the tissue anchor 750 are manually accessible from outside of the delivery device 754 by the operator. This allows the operator to use the control members 760, 762 to manipulate the tissue anchor 750 and to use the locking device 784 to unlock the control members 760, 762 from the central body 753 of the tissue anchor 750, as discussed in greater detail below.

The step 701 can further include inserting a guide wire 786 through the delivery device 754 so that the tissue anchor 750 can be guided along the guide wire 786 as the tissue anchor 750 is moved through the delivery device 754. The tissue anchor 750 is moved in the collapsed state along the guide wire 786 so that the tissue anchor 750 can be inserted into the anatomical cavity at the step 702 discussed below.

In the step 702 illustrated in FIG. 7B, the tissue anchor 750 is inserted into and positioned within the anatomical cavity 752. To push the tissue anchor 750 through the delivery device 754, a pusher (e.g., a rod) can be used. The tissue anchor 750 is further placed in a deployed state (e.g., the deployed state 450 shown in FIG. 4A) in which the tissue anchor 750 forms an opening 751 through which a medical instrument 742 (shown in FIG. 7F) can be inserted. When in the deployed state, the tissue anchor 750 can have a configuration similar to that shown for the tissue anchor 400 in FIG. 4A.

To transition from the collapsed state to the deployed state, the tissue anchor 750 can be configured to have a neutral state corresponding to the deployed state. For example, as discussed with respect to the tissue anchor 400 of FIG. 4A, the central body 753 and the tissue stabilizing arms 780a, 780b, 780c of the tissue anchor 750 can be formed of a shape memory material that biases the tissue anchor 750 toward the deployed state when the tissue anchor 750 is in the collapsed state. As the tissue anchor 750 is inserted beyond the delivery device 754 into the anatomical cavity 752 and the delivery device 754 no longer surrounds the tissue anchor 750 and no longer applies forces on the tissue anchor 750, the tissue anchor 750 is placed in the deployed state. The central body 753 and the tissue stabilizing arms 780a, 780b, 780c of the tissue anchor 750 expand radially outwardly to a configuration similar to that shown in FIG. 4A, thereby causing the tissue anchor 750 to form the opening 751 and causing the tissue stabilizing arms 780a, 780b, 780c to be in position to contact the second tissue wall 758. The tissue stabilizing arms 780a, 780b, 780c extend outwardly in response to the tissue anchor 750 being moved beyond the delivery device 754 and into the anatomical cavity 752, thus removing forces applied to the tissue anchor 750 by the internal walls of the delivery device 754.

As the tissue anchor 750 is inserted into the anatomical cavity 752, at least some portions of the control members 760, 762 and the locking device 784 are maintained outside of the anatomy so that the operator can manually access them.

In some implementations, a dilator, a balloon, or a stent is inserted, e.g., over a guide wire, through the delivery device 754 and then into the opening 751 of the tissue anchor 750 to enlarge a size of the opening 751 of the tissue anchor 750. The desired diameter can be selected based on, for example, a desired size of a workspace within the anatomical cavity 752 or a size of the medical instrument 742 to be used.

As part of the step 702, a force can be applied to a tapered distal tip 787 of the delivery device 754 to cause the distal tip 787 to form an opening 788. For example, the delivery device 754 can be a hollow puncture device, e.g., a hollow needle, and the tapered distal tip 787 can be precut such that a force applied on the distal tip 787 on a proximal surface of the distal tip 787 causes the distal tip 787 to open and form the opening 788. The opening 788 formed in this step can be sufficiently large to allow the tissue anchor 750 to pass beyond the distal tip 787 of the delivery device 754 and into the anatomical cavity 752.

To apply the force on the distal tip 787, a pushing member can be used to push on the distal tip 787. In some implementations, the pushing member for opening the distal tip 787 can be a guide wire (e.g., the guide wire 786 with varying diameters or a taper from small at the distal tip to a larger diameter more proximally or another guide wire separate from the guide wire 786), the tissue anchor 750, a dilator, or some other component that can apply a pushing force on the distal tip 787.

In implementations in which a component separate from the guide wire 786 opens the distal tip 787, after the force is applied on the distal tip 787 of the delivery device 754 to form the opening 788, the guide wire 786 is advanced through the opening 788 into the anatomical cavity 752.

Figure 7C:
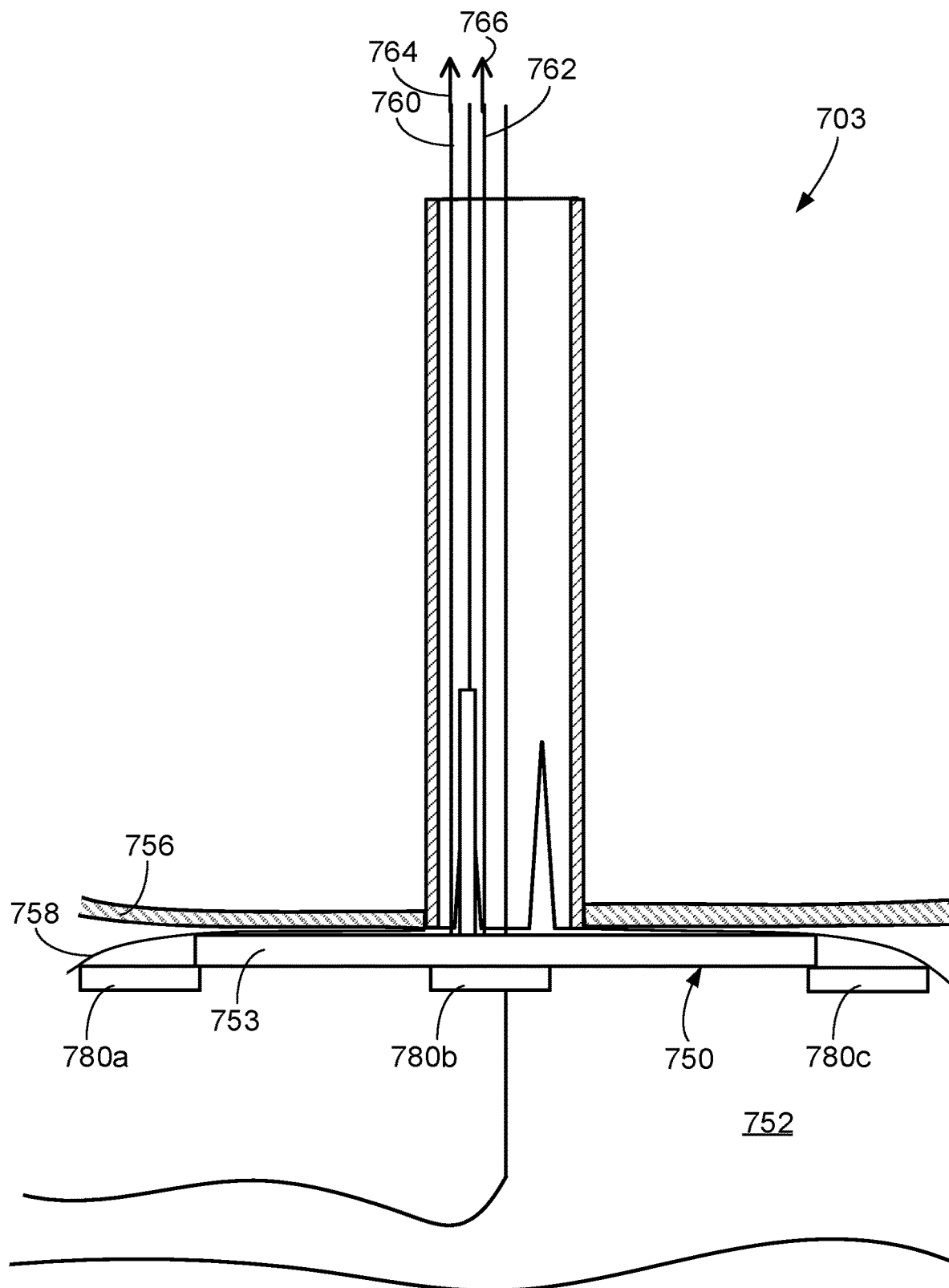
Figure 7D:
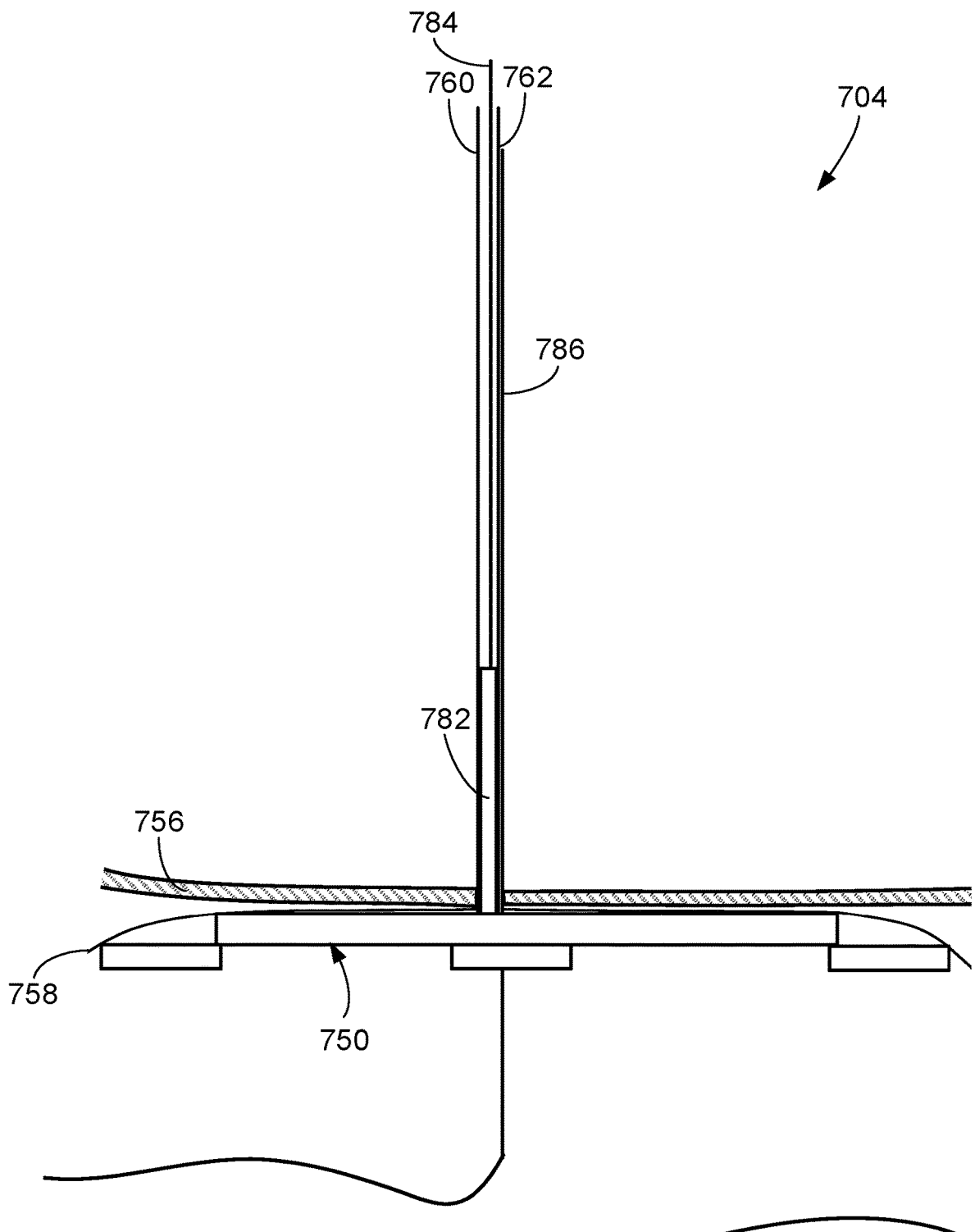
Figure 7E:
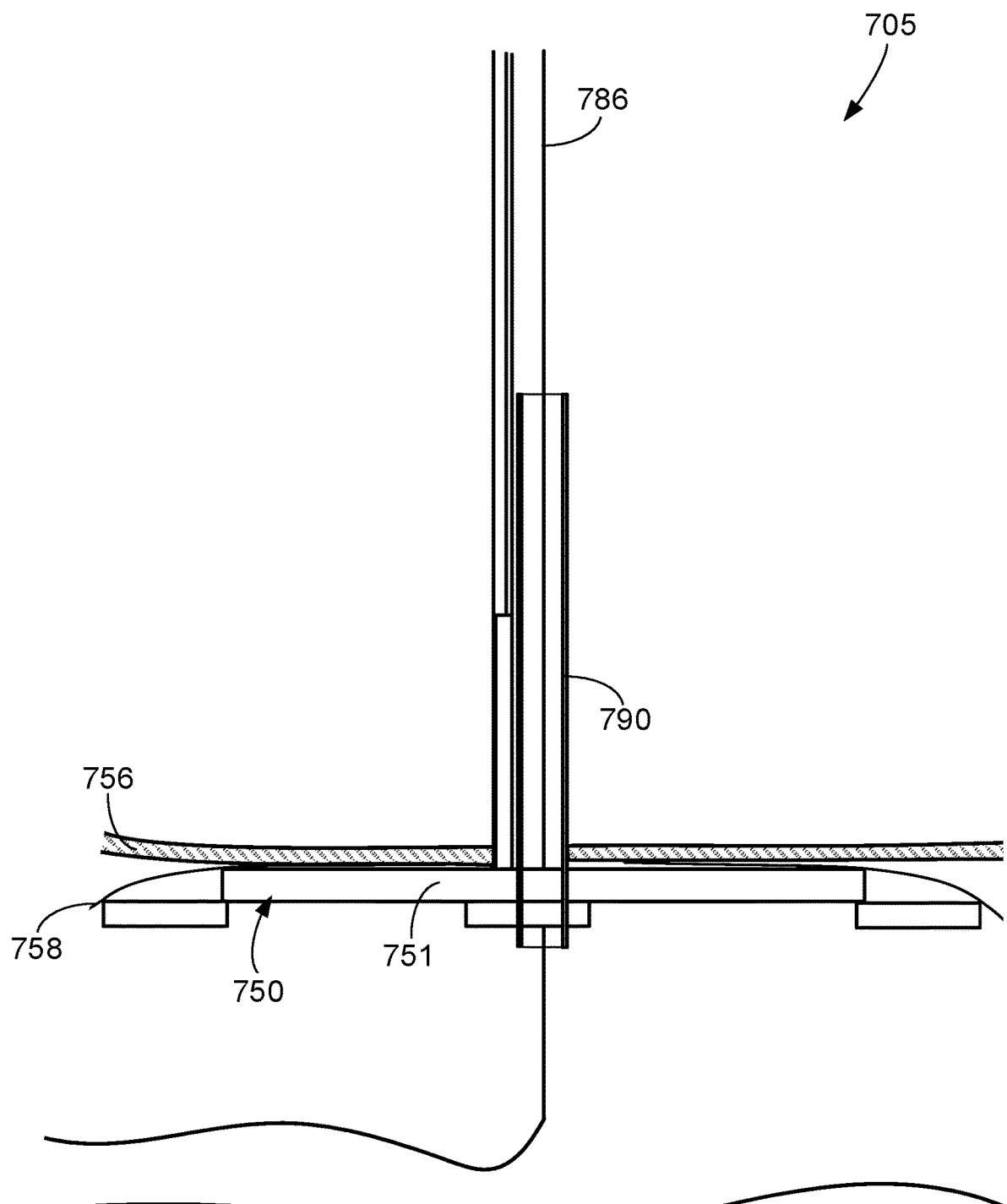

FIGS. 7C-7E illustrate steps 703-707 that correspond to steps in which the tissue anchor 750 is in engagement with the second tissue wall 758 in the deployed state of the tissue anchor 750.

In the step 703 illustrated in FIG. 7C, the tissue anchor 750 in the deployed state is caused to engage with the second tissue wall 758 to stabilize the second tissue wall 758. One or more pulling forces (e.g., pulling forces 764, 766) are applied to the tissue anchor 750 (e.g., in a direction away from the anatomical cavity 752). The central body 753 and tissue stabilizing arms 780*a*, 780*b*, 780*c* are pulled into contact with the second tissue wall 758 with the pulling forces 764, 766, and the second tissue wall 758 is pulled toward the first tissue wall 756. The tissue contact surfaces of the tissue stabilizing arms 780*a*, 780*b*, 780*c* (e.g., the tissue contact surfaces 482*a*, 482*b*, 482*c* shown in FIG. 4A) contact the second tissue wall 758. As part of the step 703, the retrieval member 782 of the tissue anchor 750 can be retracted into the access location 740 as the tissue anchor 750 is pulled by the operator. This causes at least part of the retrieval member 782 to extend outside of a body of the subject, e.g., outside of the first tissue wall 756 and the second tissue wall 758.

The tissue anchor 750 is pulled using one or more of the control members 760, 762. The control member 760, by being attached to a first lengthwise half of the central body 753 of the tissue anchor 750 (e.g., the first lengthwise half shown in FIG. 4A-4C), allows the pulling force 764 to be applied to the first lengthwise half of the central body 753 of the tissue anchor 750. And the control member 762, by being attached to a second lengthwise half of the central body 753 of the tissue anchor 750 (e.g., the first lengthwise half shown in FIGS. 4A-4C), allows the pulling force 766 to be applied to the second lengthwise half of the central body 753 of the tissue anchor 750. Pulling the second tissue wall 758 toward the first tissue wall 756 can cause a portion of the second tissue wall 758 to be pulled taut. In addition, although the delivery device 754 is depicted as being positioned at the access location 740 during the step 703, in some implementations, the delivery device 754 is removed after the tissue anchor 750 is positioned in the anatomical cavity 752, after the tissue anchor 750 is in the deployed state, and/or after the tissue anchor 750 is engaged with the second tissue wall 758.

In the step 704 illustrated in FIG. 7D, the delivery device 754 is removed. The delivery device 754 can be withdrawn through the first tissue wall 756 and the second tissue wall 758. In withdrawing the delivery device 754, the operator can leaves the tissue anchor 750 and the guide wire 786 within the anatomy. The first and second tissue walls 756, 758 can be sufficiently elastic to close around the tissue anchor 750 and the guide wire 786 when the delivery device 754 is removed. As shown in FIG. 7D, the retrieval member 782, the guide wire 786, the locking device 784, and the control members 760, 762 are all manually accessible by the operator outside of the anatomy.

In the step 705 illustrated in FIG. 7E, an instrument sheath 790 is introduced through the first tissue wall 756 and the second tissue wall 758. The instrument sheath 790 can be inserted through the opening 751 of the tissue anchor 750. The instrument sheath 790 can be placed over the guide wire 786.

Figure 7F:
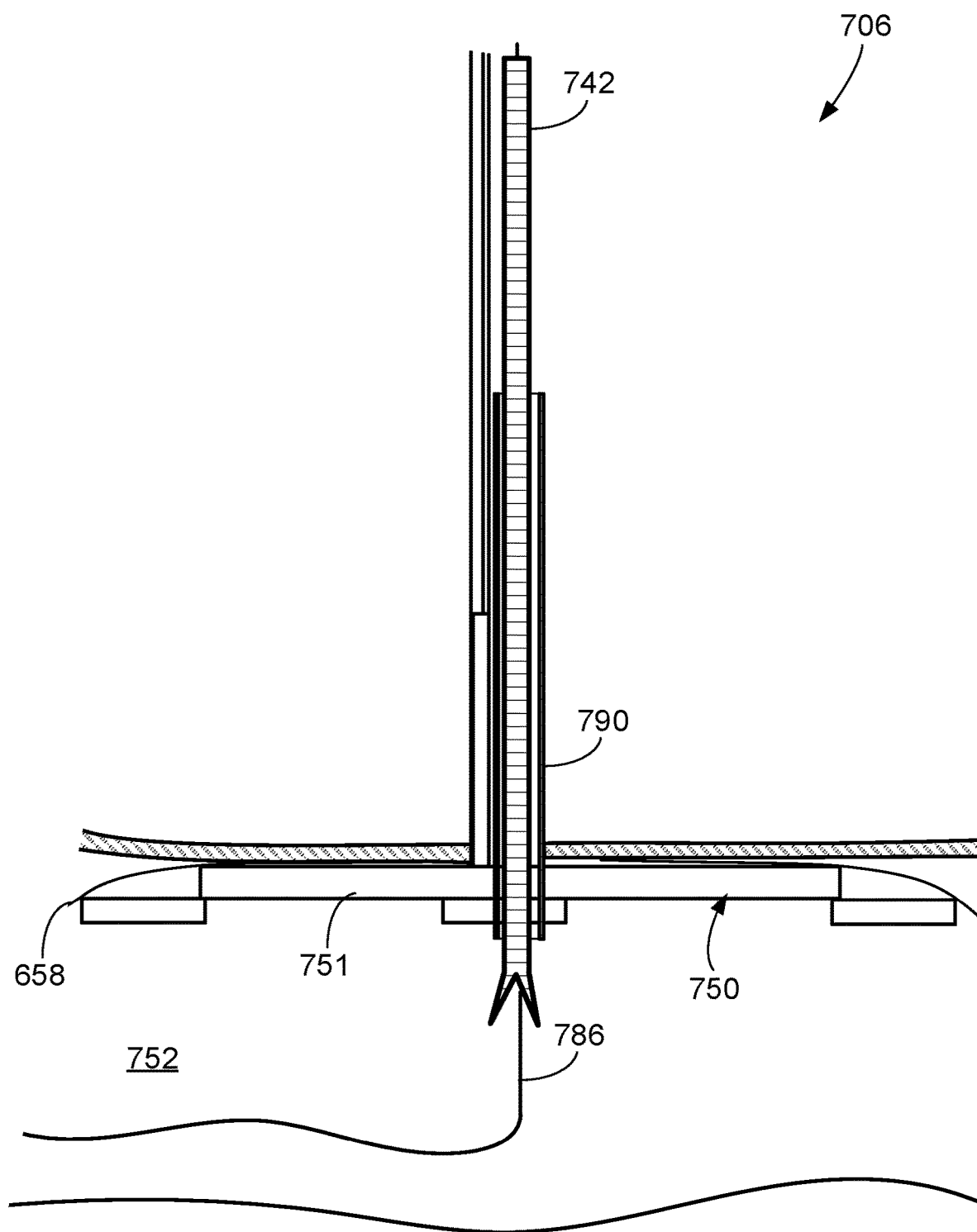

In the step 706 illustrated in FIG. 7F, at least a portion of the medical instrument 742 is delivered into the anatomical cavity 752 with the medical instrument 742 aligned with the opening 751 of the tissue anchor 750. The medical instrument 742 can be advanced along the guide wire 786 and can include a port that receives the guide wire 786. The portion of the medical instrument 742 is inserted through the instrument sheath 790. Furthermore, the portion of the medical instrument 742 is inserted through the opening 751 of the tissue anchor 750 while the tissue anchor 750 is engaged with the second tissue wall 758. This engagement between the tissue anchor 750 and the second tissue wall 758 can improve the stability of the second tissue wall 758, thereby making it easier to deliver the portion of the medical instrument 742 into the anatomical cavity 752.

Figure 7G:
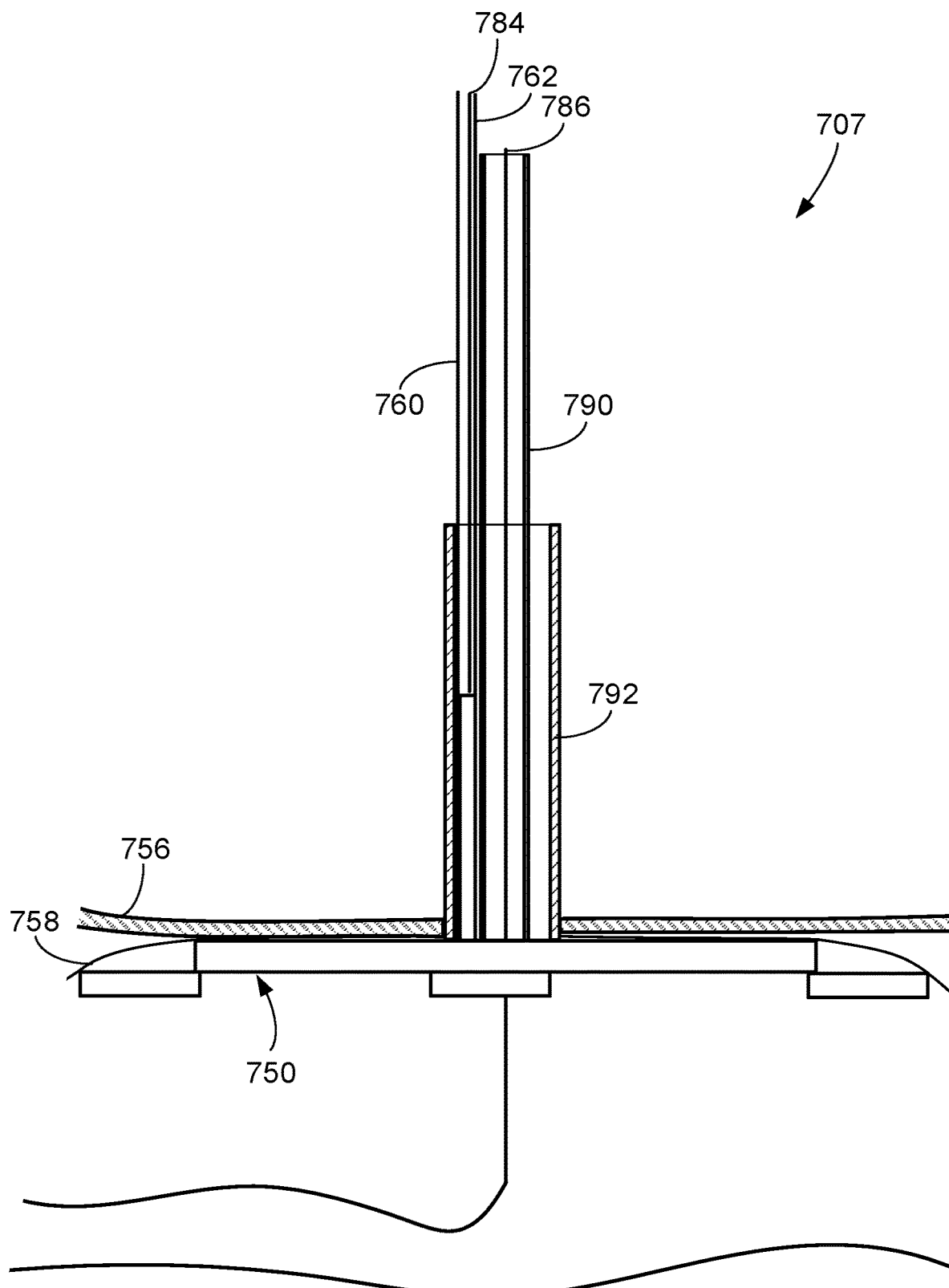

In the step 707 illustrated in FIG. 7G, a retrieval sheath 792 is introduced through the first tissue wall 756 and the second tissue wall 758 in preparation for retrieval of the tissue anchor 750 from the anatomy. The retrieval sheath 792 is placed over the retrieval member 782 of the tissue anchor 750. In some implementations, the retrieval sheath 792 is placed over all externalized components including the control members 760, 762 of the tissue anchor 750, the locking device 784 of the tissue anchor 750, the instrument sheath 790, and/or the guide wire 786.

Figure 7H:
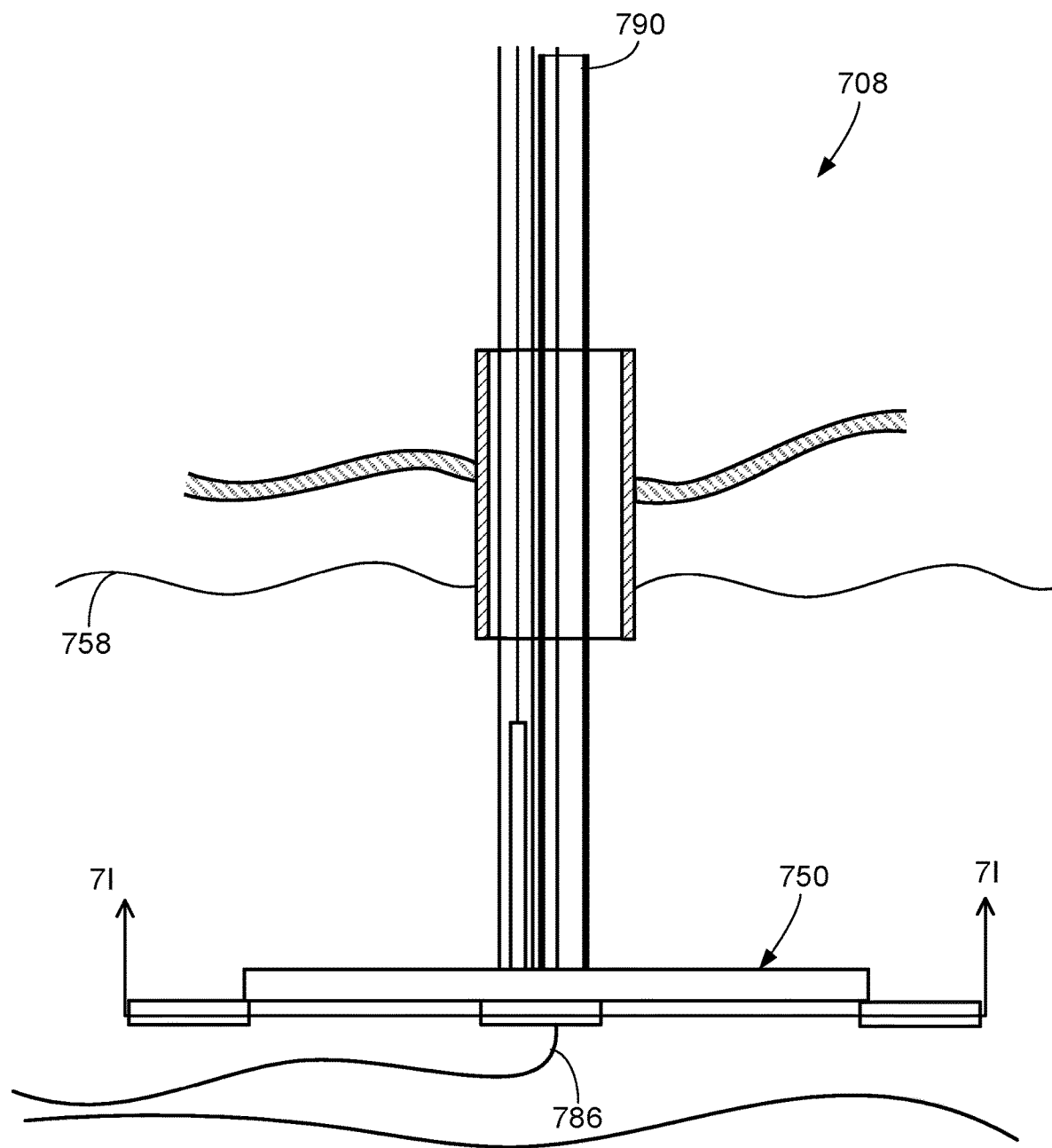

In the step 708 illustrated in FIG. 7H, the one or more pulling forces on the tissue anchor 750 are released. This causes the tissue anchor 750 to disengage from the second tissue wall 758. The medical instrument 742 and/or the instrument sheath 790, in some implementations, can be removed before the one or more pulling forces of the tissue anchor 750 are released.

Figure 7I:
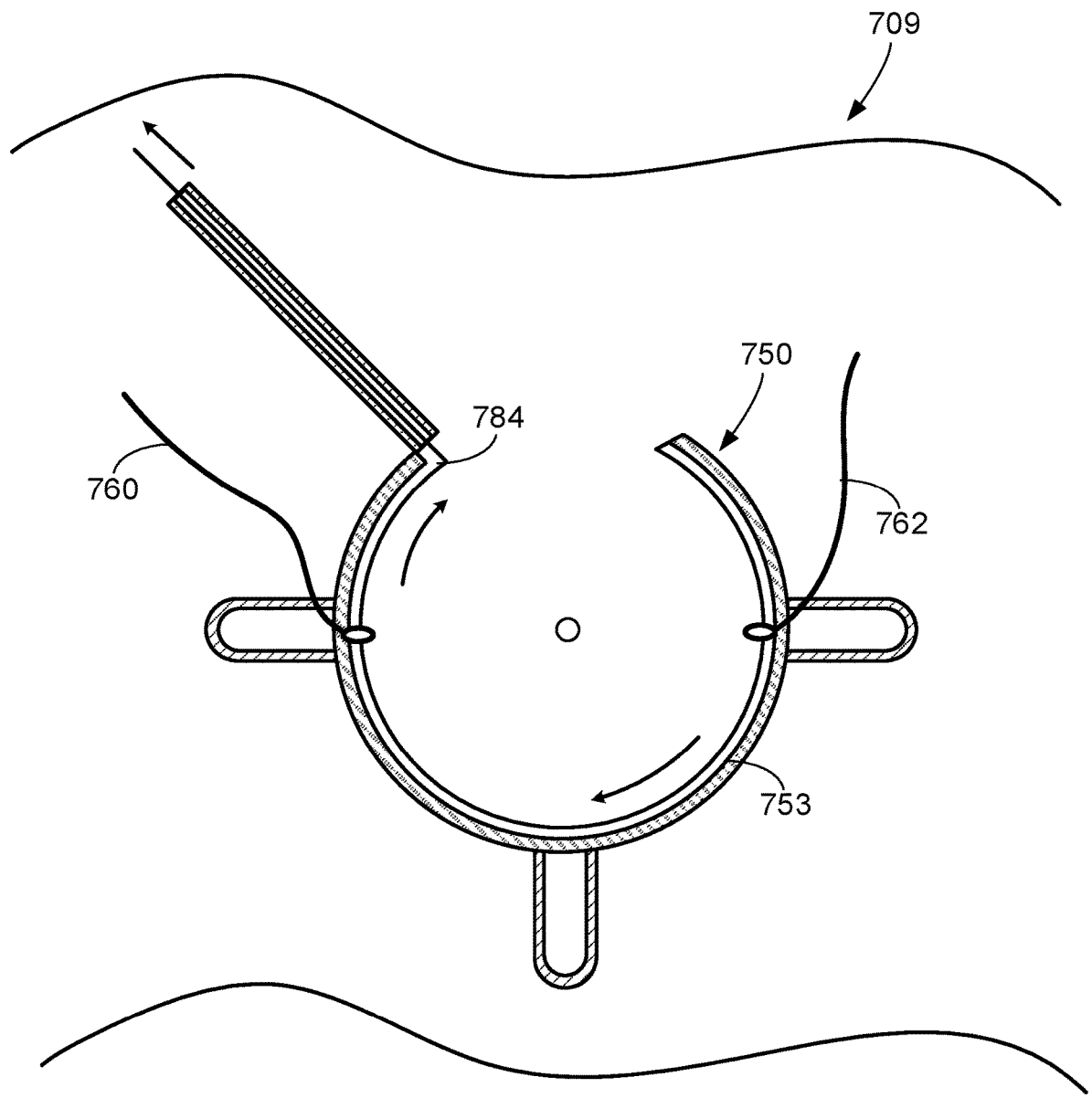

In the step 709 illustrated in FIG. 7I, the locking device 784 is operated to release the control members 760, 762 from the central body 753 of the tissue anchor 750. As discussed with respect to the tissue anchor 400 of FIGS. 4A-4C, the locking device 784 can be engaged with the control members 760, 762 to attach the control members 760, 762 to the central body 753. The locking device 784 can be pulled relative to the central body 753 to detach the control members 760, 762 from the central body 753. The control members 760, 762 can then be pulled out of the anatomy and away from the remainder of the tissue anchor 750. The locking device 784 can similarly be removed from the tissue anchor 750 and removed from the anatomy. Removing the control members 760, 762 and the locking device 784 from the tissue anchor 750 can simplify removal of the rest of the tissue anchor 750 from the anatomy and reduce the risk of entanglement of the control members 760, 762.

Figure 7J:
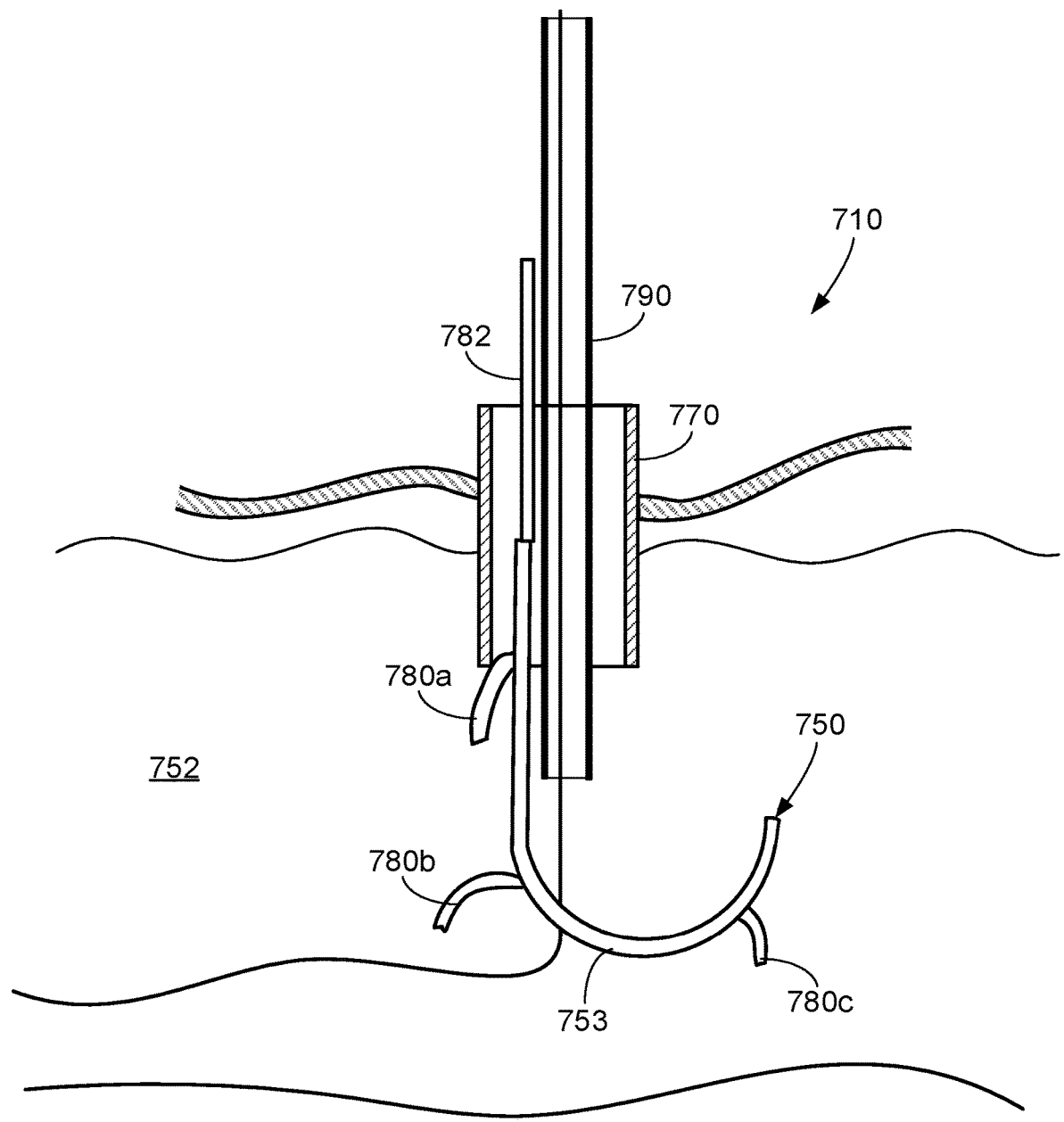

FIG. 7J illustrates a step 710 for withdrawing the tissue anchor 750 from the anatomical cavity 752. In the step 710 illustrated in FIG. 7J, the tissue anchor 750 is withdrawn from the anatomical cavity 752. The tissue anchor 750 is placed in the collapsed state (e.g., the collapsed state 440 shown in FIGS. 4B-4C) in a retrieval sheath 770. The walls of the retrieval sheath 770 can apply a force on the tissue anchor 750 as the tissue anchor 750 is pulled into the retrieval sheath 770, e.g., using the control members 760, 762. This force causes the tissue anchor 750 to transition from the deployed state (FIG. 4A) to the collapsed state (FIGS. 4B-4C). The guide wire 786 remains in the anatomical cavity 752 to allow deployment of further medical instruments into the anatomical cavity 752.

The tissue anchor 750 can be withdrawn into the retrieval sheath 770 and into the collapsed state by positioning the retrieval sheath 770 over the retrieval member 782 of the tissue anchor 750 so that the central body 753 is guided into the retrieval sheath 770. In implementations in which the instrument sheath 790 is still in the anatomy at the step 710, the retrieval sheath 770 can be further placed over the instrument sheath 790. To withdraw the tissue anchor 750 into the retrieval sheath 770, the retrieval sheath 770 is placed over the retrieval member 782, then over the first lengthwise end of the central body 753, and then over the second lengthwise end of the central body 753. As the tissue anchor 750 is withdrawn into the retrieval sheath 770, the tissue stabilizing arms 780a, 780b, 780c are deformed into the collapsed state and retracted into the retrieval sheath 770. The retrieval sheath 770 applies forces on the tissue stabilizing arms 780a, 780b, 780c and the central body 753 of the tissue anchor 750 to transition the tissue stabilizing arms 780a, 780b, 780c and the central body 753 into the collapsed state. In this transition to the collapsed state, the first lengthwise end and the second lengthwise end of the central body 753 of the tissue anchor 750 move away from one another, thereby causing the central body 753 to form a straightened structure positionable in the retrieval sheath 770.

The retrieval member 782 and the retrieval sheath 770 both include portions that are positioned outside of the anatomy and are both manually accessible by the operator. To position the retrieval sheath 770 over the retrieval member 782 of the tissue anchor 750, the operator can advance the retrieval sheath 770 toward the anatomical cavity 752 while holding the retrieval member 782 in place, pull the retrieval member 782 of the tissue anchor 750, or both advance the retrieval sheath 770 and pull the retrieval member 782.

Further Alternative Implementations

A number of implementations have been described. While this specification contains many specific implementation details, these should not be construed as limitations on the scope of what is being claimed, which is defined by the claims themselves, but rather as descriptions of features that may be specific to particular implementations of particular inventions. It will be understood that various modifications may be made.

Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially be claimed as such, one or more features from a claimed combination can in some cases be excised from the combination, and the claim may be directed to a subcombination or variation of a subcombination.

While operations are depicted in the drawings and recited in the claims in a particular order, this by itself should not be understood as requiring that such operations be performed in the particular order shown or in sequential order, or that all illustrated operations be performed, to achieve desirable results.

Retrieval sheaths 570, 670, 770 have been described with respect to the processes illustrated in FIGS. 5A-5F, 6A-6F, and 7A-7J. In some implementations, the sheath can correspond to the delivery device (e.g., the delivery device 554, 654, or 754) used to initially deliver the tissue anchor (e.g., the tissue anchor 550, 650, or 750) into the anatomical cavity. In other implementations, the sheath is a device separate from the delivery device. The sheath can be placed at the access location for withdrawal of the tissue anchor after the delivery device is removed from the access location.

Medical instruments 542, 642, 742 have been described with respect to the processes illustrated in FIGS. 5A-5F, 6A-6F, and 7A-7J. In some implementations, the medical instrument (e.g., the medical instrument 542, 642, 742) is a closure device used to perform a tissue closure procedure on the second tissue wall after a medical procedure in the anatomical cavity is completed. If the medical instrument is a closure device, the medical instrument can be a first medical instrument used to stabilize the second tissue wall and can allow for delivery of a second medical instrument to perform the medical procedure in the anatomical cavity. In this regard, the medical procedure can be performed using the second medical instrument while the first medical instrument (e.g., the closure device) is used to stabilize the second tissue wall.

In some implementations, the medical instrument (e.g., the medical instrument 542, 642, 742) is a surgical instrument used to perform the medical procedure. In this regard, the medical procedure can be a surgical procedure performed in the anatomical cavity, and the surgical procedure can be performed using the medical instrument while the tissue anchor (e.g., the tissue anchor 550, 650, 750) is used to stabilize the second tissue wall.

The medical instruments inserted through openings of the tissue anchors (e.g., the medical instruments 542, 642, 742) described in this disclosure can be used for a number of medical procedures. For example, the medical instruments can be used as part of treatment for an obstruction or stenosis (e.g., which can further involve delivery of balloons, baskets, aspiration catheters, or surgical instruments such as endoscopes); delivery of therapeutic chemicals (e.g., pharmaceuticals, biologics, drugs, radiotherapy chemicals, etc.); placement of imaging technology (e.g., which may be placed through the tissue anchor to further diagnose or plan for treatment); and delivery of biopsy devices (e.g., to sample tissue). These devices and/or chemicals can be delivered through the opening of the tissue anchor or through an access that is stabilized in part using the tissue anchor.

In implementations, the tissue walls (e.g., the tissue walls 556, 558, 656, 658, 756, 758) described as part of the processes described in this disclosure can correspond to different parts of the anatomy. The first tissue wall (e.g., the first tissue wall 556, 656, or 756) can generally include muscle and skin tissue, while the second tissue wall can include a tissue wall for a particular target organ of the anatomy. For example, in some implementations, the first tissue wall (e.g., the first tissue wall 556, 656, or 756) can correspond to an abdominal wall, and the second tissue wall (e.g., the second tissue wall 558, 658, 758) can correspond to a wall of a small intestine. In other implementations, the first tissue wall can correspond to a pelvic wall, and the second tissue wall can correspond to a urinary bladder wall. Other potential target organs include the gall bladder, the stomach, the large intestine, the kidney or any organ or structure with a hollow area that allows deployment of the tissue anchor and that requires stabilization for broader access to treat or diagnose, with the second tissue wall corresponding to an organ wall of one of these potential target organs and the first tissue wall corresponding to the overlying muscle and/or skin tissue.

Dimensions of the tissue anchor (e.g., the tissue anchors 200, 300, 400, 550, 650, 750) can vary in implementations and can vary depending on the target organ. A length of the central body of the tissue anchor, as measured from the first lengthwise end of the central body to the second lengthwise end of the central body can be between 15 and 45 millimeters (e.g., between 15 and 25 millimeters, between 25 and 35 millimeters, between 35 and 45 millimeters, etc.), no less than 15 millimeters, no less than 20 millimeters, no less than 25 millimeters, no less than 30 millimeters, no less than 35 millimeters, no less than 40 millimeters, or more. An overall width of the tissue anchor in the deployed position can be between 15 and 70 millimeters (e.g., between 15 and 40 millimeters, between 20 and 45 millimeters, between 25 and 50 millimeters, between 30 and 55 millimeters, between 35 and 60 millimeters, etc.). An overall width of the central body of the tissue anchor in the deployed position can be between 2 and 10 millimeters (e.g., between 2 and 8 millimeters, between 3 and 9 millimeters, between 4 and 10 millimeters, etc.).

Lengths of a tissue stabilizing arm (e.g., the tissue stabilizing arms 380a, 380b, 380c, 480a, 480b, 480c, 680a, 680b, 680c, 780a, 780b, 780c), as measured from the point at which the tissue stabilizing arm is attached to the central body to the distal tip of the tissue stabilizing arm, can vary in implementations. In some implementations, the length of the tissue stabilizing arm is between 1 and 15 millimeters (e.g., between 1 and 10 millimeters, between 3 and 13 millimeters, between 5 and 15 millimeters, etc.).

Angles between tissue stabilizing arms (e.g., the angles between the tissue stabilizing arms 380a, 380b, 380c, the angles between the tissue stabilizing arms 480a, 480b, 480c, the angles between the tissue stabilizing arms 680a, 680b, 680c, or the angles between the tissue stabilizing arms 780a, 780b, 780c) in the deployed state can vary in implementations. In some implementations, an angle between adjacent two of the tissue stabilizing arms can be between 30 degrees and 180 degrees, e.g., between 30 degrees and 90 degrees, between 60 degrees and 120 degrees, between 90 and 150 degrees, between 150 and 180 degrees, etc.). An angle spanned by the slot (e.g., the slot 260, the slot 568, or the slot 668) can vary in implementations. In some implementations, the slot spans an angle between 30 and 90 degrees (e.g., between 45 and 75 degrees, between 50 and 70 degrees, between 55 and 65 degrees, about 60 degrees, etc.).

In implementations, each tissue stabilizing arm (e.g., the tissue stabilizing arms 380a, 380b, 380c, 480a, 480b, 480c, 680a, 680b, 680c, 780a, 780b, 780c) extends along a corresponding longitudinal axis. In some implementations, the tissue stabilizing arm can include one or more hooks or barbs that can facilitate engagement with a tissue wall (e.g., the second tissue wall 558, 658, 758). For example, each tissue stabilizing arm can include a hook on a distal end of the tissue stabilizing arm. Alternatively or additional, each tissue stabilizing arm can include hooks or barbs spaced apart from one another along the longitudinal axis and protruding away from the longitudinal axis.

The control members (e.g., the control members 220, 230, 320, 330, 420, 430, 560, 562, 660, 662, 760, 762) are described as being used to pull the tissue anchor. In implementations, the control members can have sufficient longitudinal rigidity to be pushed in addition to pulled. For example, one or both of the control members can, in alternative implementations, be formed of a polymer or metal rod with longitudinal rigidity. The control members are attached to the central body such that the control members are at locations 180 degrees away from one another along the central body.

The delivery device (e.g., the delivery device 554, 654, 754) can vary in implementations. In some implementations, the delivery device is a puncture device as described in this disclosure. The delivery device can be a 16-gauge to 21-gauge, or larger, hollow needle.

In some implementations, the delivery device (e.g., the delivery device 554, 654, 754) can be preloaded with the tissue anchor. The tissue anchor can be preassembled within the delivery device and provided to the operator for use on a subject. In some implementations, the operator can manually load the tissue anchor into the delivery device (e.g., following the steps 501, 601, 701 described in this disclosure). In some implementations, the control members can be used by the operator to load the tissue anchor into the delivery device. In examples in which the control members have sufficient longitudinal rigidity to support a longitudinal load, the control members can be used to push the tissue anchor into the delivery device. In other implementations, the tissue anchor is loaded in a protective tube and then is removed before being placed into the delivery device.

Accordingly, other implementations are within the scope of the claims.

What is claimed is:

1. A method comprising:
    inserting a central body of a tissue anchor through a tissue wall of a patient in a collapsed state of the tissue anchor and inserting the central body of the tissue anchor into an anatomical cavity of the patient defined by the tissue wall, wherein in the collapsed state of the tissue anchor, the central body of the tissue anchor extends from a first lengthwise end to a second lengthwise end to form an elongate structure;
    placing the tissue anchor in a deployed state by causing the central body of the tissue anchor to expand outwardly and define an opening as the central body of the tissue anchor is inserted into the anatomical cavity defined by the tissue wall and by causing a plurality of stabilizing arms attached to the central body of the tissue anchor to extend radially outwardly from the central body of the tissue anchor, wherein in the deployed state of the tissue anchor, the first lengthwise end and the second lengthwise end are positioned in the anatomical cavity;

causing the central body of the tissue anchor in the deployed state of the tissue anchor to engage with the tissue wall to stabilize the tissue wall;

delivering at least a portion of a medical instrument into the anatomical cavity with the medical instrument being aligned with the opening of the tissue anchor;

withdrawing the tissue anchor from the anatomical cavity, wherein withdrawing the tissue anchor from the anatomical cavity comprises placing the tissue anchor in the collapsed state; and using the medical instrument to perform a medical procedure on the tissue wall or in the anatomical cavity.

2. The method of claim 1, further comprising:
after delivering at least the portion of the medical instrument into the anatomical cavity and before using the medical instrument to perform the medical procedure on the tissue wall or in the anatomical cavity, initiating withdrawal of the tissue anchor from the anatomical cavity such that the opening of the tissue anchor is positioned around and is moved along at least the portion of the medical instrument during the withdrawal of the tissue anchor.

3. The method of claim 2, wherein the medical instrument is a closure device, and the medical procedure is a tissue closure procedure performed on the tissue wall.

4. The method of claim 1, wherein:
delivering at least the portion of the medical instrument into the anatomical cavity with the medical instrument being aligned with the opening of the tissue anchor comprises:
inserting the portion of the medical instrument through the opening of the tissue anchor; and
using the medical instrument to perform the medical procedure on the tissue wall or in the anatomical cavity comprises:
using the medical instrument to perform the medical procedure while the portion of the medical instrument extends through the opening of the tissue anchor.

5. The method of claim 4, wherein the medical instrument is a surgical instrument, and the medical procedure is a surgical procedure performed in the anatomical cavity.

6. The method of claim 1, wherein inserting the central body of the tissue anchor through the tissue wall and inserting the central body into the anatomical cavity comprise:
inserting a puncture device through the tissue wall; and
inserting the central body of the tissue anchor through the puncture device into the anatomical cavity.

7. The method of claim 6, wherein:
inserting the central body of the tissue anchor through the tissue wall and inserting the central body into the anatomical cavity further comprises:
inserting a guide wire through the puncture device into the anatomical cavity; and
inserting the central body of the tissue anchor through the puncture device into the anatomical cavity comprises:
moving the central body of the tissue anchor in the collapsed state of the tissue anchor along the guide wire into the anatomical cavity.

8. The method of claim 7, wherein inserting the guide wire through the puncture device into the anatomical cavity comprises:

applying a force on a tip of the puncture device to cause the tip of the puncture device to form an opening; and
advancing the guide wire through the opening formed at the tip of the puncture device to insert the guide wire into the anatomical cavity.

9. The method of claim 1, wherein placing the tissue anchor in the deployed state comprises:
causing the central body of the tissue anchor to expand radially outwardly; and
causing the central body of the tissue anchor to form the opening.

10. The method of claim 9, wherein causing the central body of the tissue anchor to form the opening further comprises:
causing the central body of the tissue anchor to extend along an arc from the first lengthwise end of the central body to the second lengthwise end of the central body.

11. The method of claim 10,
wherein placing the tissue anchor in the collapsed state comprises
positioning a sheath over a retrieval member extending from the first lengthwise end or the second lengthwise end of the central body of the tissue anchor.

12. The method of claim 11, wherein in the deployed state of the tissue anchor, the central body extends along a plane, and the retrieval member extends from the first lengthwise end or the second lengthwise end of the central body along an axis substantially perpendicular to the plane.

13. The method of claim 12, wherein placing the tissue anchor in the collapsed state comprises:
causing the first lengthwise end and the second lengthwise end of the central body to move away from one another, thereby causing the central body to form the elongate structure positionable in the sheath.

14. The method of claim 13, wherein:
the axis is a first axis;
the central body extends along a second axis in the collapsed state of the tissue anchor; and
placing the tissue anchor in the collapsed state comprises:
causing the plurality of tissue stabilizing arms attached to the central body to extend parallel to the second axis along which the central body extends in the collapsed state of the tissue anchor.

15. The method of claim 1, wherein the plurality of tissue stabilizing arms comprises at least three tissue stabilizing arms.

16. The method of claim 1, further comprising:
after placing the tissue anchor in the deployed state and before causing the tissue anchor in the deployed state to engage with the tissue wall, enlarging a size of the opening of the tissue anchor.

17. The method of claim 1, wherein causing the tissue anchor in the deployed state to engage with the tissue wall comprises:
applying a pulling force on the central body of the tissue anchor to cause the tissue anchor to be pulled against the tissue wall.

18. The method of claim 17, wherein the pulling force is a first pulling force applied on a first lengthwise half of the central body, and wherein causing the tissue anchor in the deployed state to engage with the tissue wall comprises:
applying, while applying the first pulling force on the central body, a second pulling force on a second lengthwise half of the central body to cause the tissue anchor to be pulled against the tissue wall.

19. The method of claim 17, wherein:
applying the pulling force on the central body to cause the tissue anchor to be pulled against the tissue wall comprises:
pulling a control member locked to the central body via a locking wire extending along the central body; and
the method further comprises:
removing the locking wire from the tissue anchor to release the control member from the central body;
removing the control member from the tissue anchor; and then
withdrawing the tissue anchor from the anatomical cavity.

* * * * *